US009874539B2

(12) United States Patent
Hu et al.

(10) Patent No.: US 9,874,539 B2
(45) Date of Patent: Jan. 23, 2018

(54) ION-SELECTIVE ELECTRODES AND REFERENCE ELECTRODES WITH A SOLID CONTACT HAVING MESOPOROUS CARBON

(71) Applicant: Regents of the University of Minnesota, Minneapolis, MN (US)

(72) Inventors: Jinbo Hu, Minneapolis, MN (US); Philippe Buhlmann, Minneapolis, MN (US); Andreas Stein, St. Paul, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 134 days.

(21) Appl. No.: 14/716,564

(22) Filed: May 19, 2015

(65) Prior Publication Data

US 2015/0338367 A1    Nov. 26, 2015

Related U.S. Application Data

(60) Provisional application No. 62/002,526, filed on May 23, 2014.

(51) Int. Cl.
*G01N 27/414* (2006.01)
*G01N 27/333* (2006.01)
(Continued)

(52) U.S. Cl.
CPC ......... *G01N 27/333* (2013.01); *G01N 27/406* (2013.01); *G01N 27/4035* (2013.01); *G01N 27/414* (2013.01)

(58) Field of Classification Search
CPC ............. G01N 27/333; G01N 27/4035; G01N 27/414; G01N 27/406
See application file for complete search history.

(56) References Cited

U.S. PATENT DOCUMENTS

| 5,312,537 A * | 5/1994 | Harrison ............ G01N 27/4035 204/416 |
| 2011/0183841 A1* | 7/2011 | Gadkaree ............... H01G 11/34 502/425 |
| 2012/0181184 A1* | 7/2012 | Whitesides ............. B01L 3/502 205/775 |

OTHER PUBLICATIONS

C.-Z. Lai, et al. "Highly Selective Detection of Silver in the Low ppt Range with Ion-Selective Electrode Based on Ionophore-Doped Fluorous Membranes" Analytical Chemistry, vol. 82, No. 18, Sep. 15, 2010, p. 7634-7640.*

(Continued)

*Primary Examiner* — J. Christopher Ball
(74) *Attorney, Agent, or Firm* — Westman, Champlin & Koehler, P.A.; Z. Peter Sawicki; Visala C. Goswitz

(57) ABSTRACT

The present description discloses solid-contact (SC) electrodes that use mesoporous carbon such as colloid-imprinted mesoporous (CIM) carbon as the interlayer. The electrodes can be ion-selective electrodes (ISEs) or reference electrodes. The CIM carbon with the interconnected mesopores is used as the intermediate layer between the solid electron conductor, such as gold, and a membrane such as an ionophore-doped ion-selective membrane or a reference membrane. The disclosure includes methods of constructing solid contact electrodes such as SC-ISE or reference electrodes with a CIM carbon interlayer, and methods of using the electrodes to determine the quantity of an analyte in a sample. The description also includes disposable paper-based devices for measuring analytes in a sample.

32 Claims, 12 Drawing Sheets

(51) Int. Cl.
   *G01N 27/406* (2006.01)
   *G01N 27/403* (2006.01)

(56) References Cited

OTHER PUBLICATIONS

A. Stein, et al. "Morphologicla Control in Colloidal Crystal Templating of Inverse Opals, Hierarchical Structures, and Shaped Particles" Chemistry of Materials, vol. 20, 2008, p. 649-666.*
Bakker, E.; Bühlmann, P.; Pretsch, E. "Carrier-Based Ion-Selective Electrodes and Bulk Optodes. 1. General Characteristics" Chem. Rev. 1997, 97, 3083-3132.
Bobacka, J. et al. "Single-Piece All-Solid-State Ion-Selective Electrode" Anal. Chem. 1995, 67, 3819-3823.
Bobacka, J.; Ivaska, A.; Lewenstam, A. "Potentiometric Ion Sensors" Chem. Rev. 2008, 108, 329-351.
Bobacka et al. "All solid-state Poly(vinyl chloride) Membrane Ion-Selective Electrodes with Poly(3-octylthiophene) Solid Internal Contact" Analyst, Sep. 1994, vol. 119, 1985-1991.
Bühlmann, P.; Chen, L. D. "Ion-Selective Electrodes with Ionophore-Doped Sensing Membranes" Supramolecular Chemistry: From Molecules to Nanomaterials, Jonathan W. Steed, P. A. G., Ed.; John Wiley & Sons, Ltd: New York, NY, 2012.
Bühlmann et al. "Carrier-Based Ion, , Selective Electrodes and Bulk Optodes. 2. Ionophores for Potentiometric and-Optical Sensors" Chem. Rev. 1998, 98, 1593-1687.
Cadogan, A. et al. "All-Solid-State Sodium-Selective Electrode Based on a Calixarene Ionophore in a Poly(vinyl chloride) Membrane with a Polypyrrole Solid Contact" Anal. Chem. 1992, 64, 2496-2501.
Cattrall, R.W. et al. "Coated Wire Ion Selective Electrodes" Analytical Chemistry, vol. 43, No. 13, 1971.
Chen et al. "Fluorous Membrane Ion-Selective Electrodes for Perfluorinated Surfactants: Trace-Level Detection and in Situ Monitoring of Adsorption" Anal. Chem. 2013, 85, 7471-7477.
Crespo et al. "Ion-Selective Electrodes Using Carbon Nanotubes as Ion-to-Electron Transducers" Anal. Chem. 2008, 80, 1316-1322.
Crespo et al. "Transduction Mechanism of Carbon Nanotubes in Solid-Contact Ion-Selective Electrodes" Anal. Chem. 2009, 81, 676-681.
Fibbioli, M. et al. "Potential Drifts of Solid-Contacted Ion-Selective Electrodes Due to Zero-Current Ion Fluxes Through the Sensor Membrane" Electroanalysis 2000, 12, 1286-1292.
Fouskaki et al. "Fullerene-based electrochemical buffer layer for ion-selective electrodes" The Analyst, 2008, 133, 1072-1075.
Fierke et al. "Effects of Architecture and Surface Chemistry of Three-Dimensionally Ordered Macroporous Carbon Solid Contacts on Performance of Ion-Selective Electrodes" Anal. Chem. 2010, 82, 680-688.
Hernández et al. "Reduced Graphene Oxide Films as Solid Transducers in Potentiometric All-Solid-State Ion-Selective Electrodes" J. Phys. Chem., 2012, 116, 22570-22578.
Johnson, R. D.; Bachas, L. "Ionophore-based ion-selective potentiometric and optical sensors" Anal. Bioanal. Chem. 2003, 376, 328-341.
Lai, C.-Z. et al. "Ion-Selective Electrodes with Three-Dimensionally Ordered Macroporous Carbon as the Solid Contact" Anal. Chem. 2007, 79, 4621-4626.
Lai et al. "Subnanomolar detection limit application of ion-selective electrodes with three-dimentionally ordered macroporous (3DOM) carbon solid contacts" J Solid State Electrochem 2009, 13:123-128.
Li et al. "All-solid-state potassium-selective electrode using graphene as the solid contact" Analyst, 2012, 137, 618.
Lindner, E.; Gyurcsányi, R.E. "Quality control criteria for solid-contact, solvent polymeric membrane ion-selective electrodes" J. Solid State Electrochem. 2009, 13, 51-68.
Michalska, A. "All-Solid-State Ion Selective and All-Solid-State Reference Electrodes" Electroanalysis 2012, 24, 1253-1265.
Ping et al. "Development of an all-solid-state potassium ion-selective electrode using graphene as the solid-contact transducer" Electrochemistry Communications 13, 2011, 1529-1532.
Pretsch, E. "The new wave of ion-selective electrodes" Trends in Analytical Chemistry, vol. 26, No. 1, 2007.
Vázquez, M. et al. "Influence of oxygen and carbon dioxide on the electrochemical stability of poly(3,4-ethylenedioxythiophene) used as ion-to-electron transducer in all-solid-state ion-selective electrodes" Sens. Actuators, B 2002, 82, 7-13.

* cited by examiner

ION-SELECTIVE ELECTRODES AND REFERENCE ELECTRODES WITH A SOLID CONTACT HAVING MESOPOROUS CARBON

CROSS REFERENCE TO RELATED APPLICATION

The present application is based on and claims the benefit of U.S. provisional patent application Ser. No. 62/002,526, filed May 23, 2014, the content of which is hereby incorporated by reference in its entirety.

FIELD

The present invention relates to electrochemical sensors and more specifically to solid-contact ion-selective electrodes and solid-state reference electrodes.

BACKGROUND

Ion-selective electrodes (ISEs) are widely used in various application fields, including clinical analysis, process control, and environmental monitoring (Bakker et al. 1997; Bühlmann et al. 1998; Bobacka et al. 2008; Bühlmann et al. 2012; Johnson et al. 2003). To achieve sensor miniaturization, small sample volumes, easy maintenance, and scalability for mass production, solid-contact ion-selective electrodes (SC-ISEs), in which a solid contact is used as the ion-to-electron transducer, have attracted much attention (Bobacka et al. 2008; Linder et al. 2009; Michalska 2012; Pretsch 2007). In view of the need for affordable and portable analytical devices for small sample volumes, miniaturizable SC-ISEs are highly desirable but are only meaningful if the reference electrode is also miniaturized.

The first proposed SC-ISE, the coated-wire electrode was extremely simple but unreliable due to the ill-defined interfacial potential between the ion-selective membrane (ISM) and the underlying conducting metal (Cattrall et al. 1971). To stabilize this interfacial potential, intermediate layers consisting of conducting polymers with high redox capacitance, such as derivatives of polypyrrole, polythiophene, and polyaniline, were introduced (Cadogan et al. 1992; Bobacka et al. 1994; Bobaca et al. 1995). Some of these sensors have shown interference from gases or are affected by the build-up of an unintended water layer between the ion-selective membrane (ISM) and the solid contact (Vazquez et al. 2002; Fibbioli et al. 2000). More importantly, since these conducting polymers are polydisperse and exhibit a continuum of local geometries, they do not have a well-defined redox potential. Consequently, it is difficult to obtain high device-to-device reproducibility and to minimize long-term drift due to reactions of the conducting polymer with ambient redox-active species such as oxygen.

Conventional reference electrodes are typically Ag/AgCl or $Hg/Hg_2Cl_2$ half cells and are connected to the sample through a salt bridge. The latter usually contains an aqueous solution of an equitransferent salt that minimizes the liquid junction potential at the interface of the bridge electrolyte and the sample. Although very stable and reliable, such reference electrodes exhibit disadvantages owing to the presence of the salt bridge, such as the need for frequent maintenance, a large size, and the mutual contamination of the bridge electrolyte and sample.

More recently, nanostructured carbon materials such as three-dimensionally ordered macroporous (3DOM) carbon, carbon nanotubes, fullerene, and graphene have gained the attention of electrochemists due to their intrinsic hydrophobicity and electric conductivity (Lai et al. 2007; Fierke et al. 2010; Crespo et al. 2008, 80; Crespo et al. 2008, 81; Fouskaki et al. 2008; Ping et al. 2011; Hernindez et al. 2012; Li et al. 2012). SC-ISEs based on these carbon materials have exhibited few problems with water layer formation and interference by $O_2$, $CO_2$, or light. Among the sensors with one of these carbon materials as an interlayer, the 3DOM carbon-based SC-ISEs have shown the most favorable long-term potential stability, which can be explained by the high capacitance of the interface between this carbon material and the ISM.

3DOM carbon consists of a glassy carbon skeleton with interconnected macropores that can be infiltrated with the ISM to form a bicontinuous ion- and electron-conducting structure. Its large interfacial contact area and high capacitance lead to excellent long-term stability of 3DOM carbon-based SC-ISEs, with a drift as low as 11.7 µV/h (Lai et al. 2007; Fierke et al. 2010). With these sensors, a subnanomolar detection limit of $Ag^+$ and trace-level detection of perfluorinated surfactants in lake water have been achieved (Lai et al. 2009; Chen et al. 2013). However, 3DOM carbon prepared from resorcinol-formaldehyde precursors contains significant amounts of redox-active surface functional groups that can affect the reproducibility of the calibration curve intercept, $E°$. As a consequence, SC-ISEs that use 3DOM carbon still require calibration. Moreover, the monolithic nature of 3DOM carbon as used in the past is problematic in view of mass production of sensors (Fierke et al. 2010).

SUMMARY

In a first aspect, the present invention relates to solid-contact (SC) electrodes that include a solid electron conductor, an interlayer comprising mesoporous carbon, and a membrane, wherein the interlayer is in contact with the conductor and the membrane. The mesoporous carbon may be colloid-imprinted mesoporous carbon (CIM carbon) that may be imprinted with colloidal silica. The electrode can be an ion-selective electrode (ISE) or a reference electrode. An ISE includes an ion-selective membrane. A reference electrode may include a reference membrane. The average diameter of the mesopores in the CIM carbon may be between about 2 nm and about 50 nm and more preferably about 15 to 50 nm. The solid electron conductor may include gold, platinum, silver, copper, stainless steel, carbon, indium-tin-oxide (ITO), fluorine-doped tin oxide (FTO) or aluminum. The ion-selective membrane may be ionophore-doped and the solid contact ion selective electrode may be calibration-free.

In another aspect, the present invention relates to an electrochemical sensor system that includes one or more solid-contact electrodes that include mesoporous carbon, preferably colloid-imprinted mesoporous carbon (CIM carbon). The solid-contact electrodes may not require calibration. The system may include 2, 3 or 4 electrodes. The electrodes can include one or more SC-ISEs and/or an SS-reference electrode. The average diameter of the mesopores in the CIM carbon may be between about 2 nm and about 50 nm and more preferably between about 15 nm and about 50 nm. The solid electron conductor may include gold, platinum, silver, copper, stainless steel, carbon, indium-tin-oxide (ITO), fluorine-doped tin oxide (FTO) or aluminum. In a SC-ISE, the ion-selective membrane may be ionophore-doped. In a solid state (SS)-reference electrode, the reference membrane can include an ionic liquid with/without a hydrophobic redox couple. A SS-reference electrode can include a hydrophobic redox couple. The electrochemical sensor system may be a potentiometric sensor, an ion-sensitive field effect transistor, a voltammetric sensor, an amperometric sensor, a coulometric sensor or an impedance sensor. The electrochemical sensor system may be a paper-based system.

In a further aspect, the present invention includes a method of making a solid-contact electrode that includes forming an interlayer comprising mesoporous carbon, preferably CIM carbon over a solid electron conductor, and placing an ion-selective membrane over the interlayer wherein the interlayer is disposed between and in contact with the solid electron conductor and the ion-selective membrane. The carbon interlayer may be a film with a thickness between about 0.5 µm and about 1000 µm, preferably between about 50 µm and about 250 µm. The solid electron conductor may include gold, platinum, silver, copper, stainless steel, carbon, indium-tin-oxide (ITO), fluorine-doped tin oxide (FTO) or aluminum. The electrode can be an ISE that includes an ion-selective membrane that can be ionophore-doped. The ion-selective membrane may be, for example, valinomycin doped. The electrode can be a SS-reference electrode that includes a solid conductor, a CIM carbon interlayer and a reference membrane. The method of forming the interlayer may include making a suspension of the CIM carbon powder and using the suspension of the CIM carbon to form a thin film over a solid electron conductor. The colloidal imprinting material may include colloidal silica.

In yet a further aspect, the present invention relates to a method of measuring an analyte in a sample. The method includes placing a sample in contact with an ion-selective electrode in an electrochemical system. The ion-selective electrode may be an SC-ISE that includes mesoporous carbon, preferably a CIM carbon interlayer. The SC-ISE further includes a solid electron conductor and ion-selective membrane wherein the CIM carbon interlayer is disposed between the solid electron conductor and the ion-selective membrane. The electrochemical system used to measure the analyte may also have a reference electrode that is a SS-reference electrode. The SS-reference electrode includes a solid electron conductor and a reference membrane wherein a CIM carbon interlayer is disposed between the solid electron conductor and the reference membrane. The analyte may be in a clinical sample, in an industrial sample, agricultural sample, or in an environmental sample. The electrochemical sensor may be a potentiometric sensor, a voltammetric sensor, an ion-sensitive field effect transistor, an amperometric sensor, a coulometric sensor or an impedance sensor. The solid electron conductor may include gold and may be a gold disk.

In another aspect, the present invention relates to a paper-based electrochemical system. The paper-based electrochemical system includes an ion-selective electrode and a solid-state reference electrode wherein the reference electrode comprises CIM carbon and a reference membrane. The paper-based system includes a stencil-printed ion-selective electrode. The stencil-printed electrode can be a Ag/AgCl electrode. The analyte to be measured may be chloride. The paper-based system includes a barrier for containing aqueous solutions, a sample compartment in contact with the reference membrane and the stencil printed electrode. The paper-based system may also include a SS-reference electrode and a SC-ion-selective electrode.

BRIEF DESCRIPTION OF THE DRAWINGS

FIG. 2A is a cyclic voltammogram obtained with a scan rate of 0.5 mV/s. FIG. 2B is chronopotentiometry data obtained with a constant current of 0.1 mA. FIG. 2C is an electrochemical impedance spectrum (EIS). The actual data is shown as the solid circles, and the solid line represents the data fit. The proposed equivalent circuit is shown in the inset.

FIG. 14a is a photograph of a device with a Ag/AgCl ISE and a Ag/AgCl reference electrode. FIG. 14b is a photograph of a device with a Ag/AgCl ISE and a reference electrode with a reference membrane. FIG. 14c is a photograph of a device containing a Ag/AgCl ISE and a CIM carbon-based reference electrode with a reference membrane.

DETAILED DESCRIPTION OF ILLUSTRATIVE EMBODIMENTS

The present description includes electrodes with mesoporous carbon as an interlayer between a solid electron conductor and a membrane. The electrode may be a solid-contact ion-selective electrode (SC-ISE) that uses mesoporous carbon as the intermediate layer or interlayer between a solid electron conductor and an ion-selective membrane (ISM). The electrode may be a solid-state (SS) reference electrode that uses mesoporous carbon as the interlayer between a solid electron conductor and a reference membrane (RM). The SC-ISE and/or the SS-reference electrode can be part of electrochemical sensing devices.

Preferably, the mesoporous carbon is colloid-imprinted mesoporous (CIM) carbon prepared from mesophase pitch. The use of CIM carbon as the interlayer in the electrodes can be advantageous due to the high surface area giving the resulting electrochemical devices a high capacitance and thereby, a large resistance to potential drift. This can result in an exceptionally high long-term stability of the sensor signal. CIM carbon also lacks the high concentration of surface functional groups and other impurities characteristic of many other high surface area carbon materials. The characteristics provided by the incorporation of the CIM carbon in the electrodes can lead to electrodes or sensors that may not require calibration.

The present description also includes an electrochemical sensing system or device. This system can include, for example, SC-ISE, a sample holder and circuitry and equipment to measure, record and/or compute the information generated from the sample analyses to identify the quantity or concentration of an analyte in the sample. The system may also include a SS reference electrode. The system can include multiple electrodes, preferably 2-4 electrodes. The present description also includes methods of making electrodes using a mesoporous carbon interlayer and also methods for using the electrodes with the mesoporous carbon interlayer for determining the quantity or concentration of an analyte in a sample.

In an exemplary embodiment, the electrochemical sensing system is a disposable paper-based potentiometric sensing device. The paper-based system includes a SS reference electrode and a stencil-printed ion selective electrode as further described below. The paper-based system may also include a SC-ISE as described herein.

"Solid-contact" and "solid-state" as referred to herein are equivalent and will be used interchangeably.

Figure 1A:
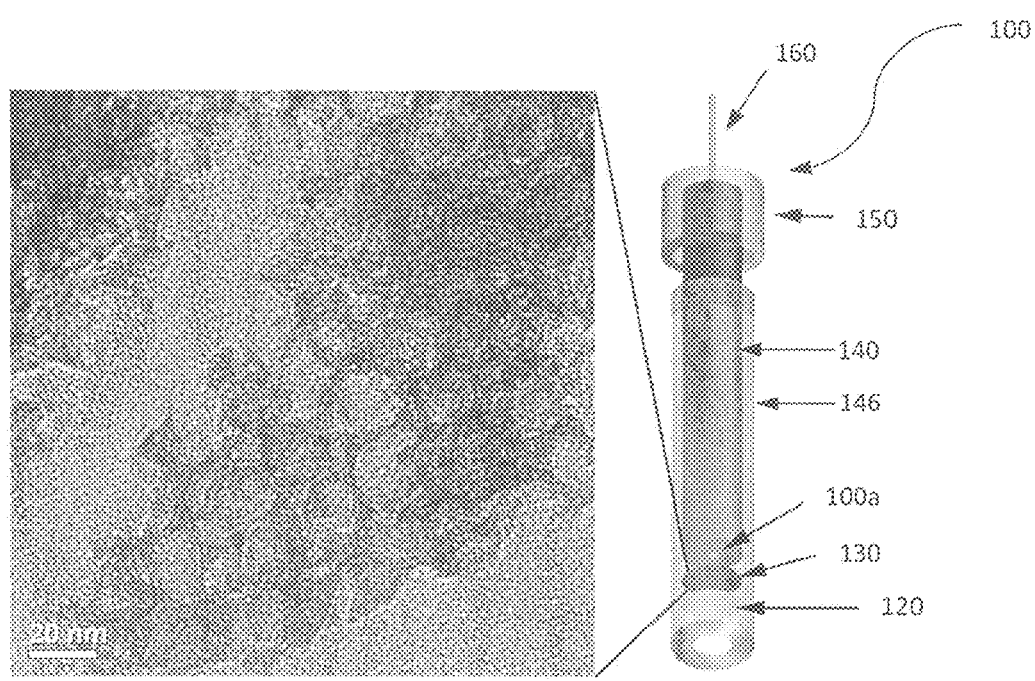
FIG. 1A is a schematic diagram of a CIM carbon-based electrode with a TEM image showing the interconnected mesopores of CIM carbon. CIM carbon is used as an intermediate layer between the gold electrode and the membrane.
Figure 7:
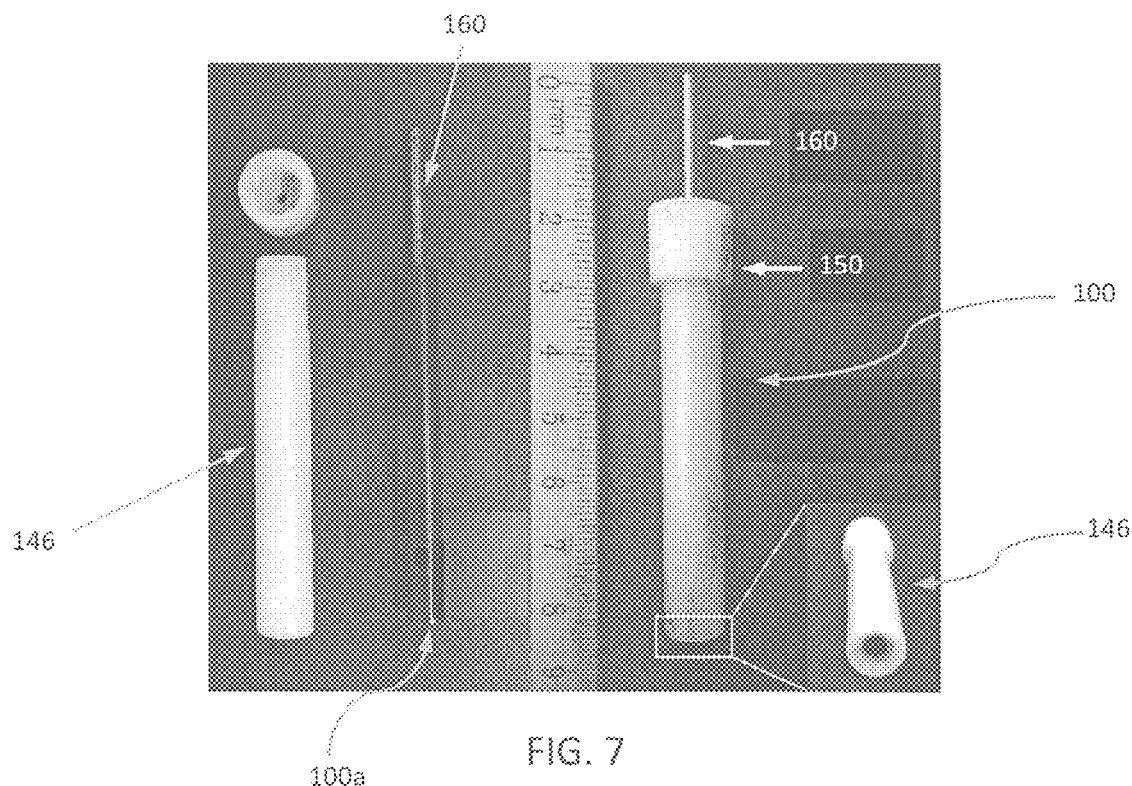
FIG. 7 is a photograph of a disassembled (left) and assembled (right) electrode setup including a gold electrode, a custom-made cylindrical electrode body, and a screw cap. The inset is a bottom view of the assembled electrode showing the ISE membrane with the CIM carbon film.

FIG. 1A is a schematic of an exemplary embodiment of electrochemical sensors described herein with an electrode including a mesoporous carbon interlayer. FIG. 7 is a photographic picture of electrode 100. Electrode 100 includes solid electron conductor 100a at the distal end. Electrode 100 also includes membrane 120 and interlayer 130. Membrane 120 may be an ion-selective membrane (ISM) or a reference membrane. In embodiments where electrode 100 is an ISE, then membrane 120 is an ISM. Alternatively, in embodiments where electrode 100 is a reference electrode, the membrane 120 is a reference membrane. Interlayer 130 is disposed between conductor 100a and membrane 120. In some embodiments, solid electron conductor 100a is a disk, for example, a gold disk. Electrode 100 may also include electrode body 140. Electrode body 140, conductor 100a, interlayer 130, membrane 120 may all be housed in housing 146 that includes screw cap 150. In one embodiment, housing 146 and screw cap 150 can be plastic housing fabricated to house the components of electrode 100. When screw cap 150 is fastened to housing 146, conductor 110a, interlayer 130 and membrane 120 come into operable contact. Electrode 100 also includes electrode connector 160 connecting conductor 100a to a recording device or computer that can record the information from electrode 100.

Solid electron conductor 100a can include a variety of conducting materials. Exemplary conducting materials include gold, silver, platinum, copper, stainless steel, carbon, indium-tin-oxide (ITO), fluorine-doped tin oxide (FTO), aluminum and the like. In one preferred embodiment, electrode 100 includes a gold disk as conductor 100a. The thickness and the diameter of the conductor can vary. The gold disk, for example, can have a diameter of between about 0.5 mm and about 5 mm. Diameters outside of this range are also within the scope of this invention. In one preferred embodiment, the diameter of the gold disk is about 2 mm.

The present description can include a SC-ISE with a mesoporous carbon interlayer, preferably a CIM carbon interlayer. A SC-ISE can be prepared with an ion-selective ionophore-doped, polymeric membrane. A SC-ISE includes a solid electron conductor, an interlayer comprising mesoporous carbon, and an ion-selective membrane including a polymer. A combination of a plasticizer, a salt, and an ionophore can also be included in the SC-ISE.

The present description can include a SS-reference electrode with a mesoporous carbon interlayer, preferably a CIM carbon interlayer. A SS-reference electrode with a polymeric reference membrane can be prepared in a manner similar to those of ion-selective electrodes described herein. A SS-reference electrode with an interlayer of mesoporous carbon includes a solid electron conductor, an interlayer including mesoporous carbon, and a polymeric reference membrane including a polymer and a hydrophilic ionic liquid with/without a hydrophobic redox couple. The measurement with a SS-reference electrode can be calibration-free. A hydrophobic redox couple is preferably used in a calibration-free measurements with a SS-reference electrode.

The size and/or shape of the electrodes can vary depending on the specific use and all are within the scope of this invention. The electrodes may be configured for home or point-of-care use, for use at a hospital, clinic or other similar settings. This may include miniaturization of the electrodes. The electrodes, for example, can be a planar device in which the solid electron conductor, an interlayer comprising mesoporous carbon, and a membrane are applied as consecutive layers on an inert substrate, such as plastic, silicon or paper. The electrodes may be paper-based systems. These paper-based systems may be disposable and miniaturized.

Electrodes described herein generally include an interlayer disposed over and in contact with the solid electron conductor. In preferred embodiments, electrodes include mesoporous carbon and in more preferred embodiments, electrodes include CIM carbon as the interlayer disposed over the conductor. CIM carbon can exhibit open and interconnected pores that can form a bicontinuous ion- and electron-conducting structure. CIM carbon may be synthesized by employing a colloidal imprinting method.

During the synthesis of CIM carbon, colloidal materials such as colloidal silica are preferably used as the template and mesophase pitch as the carbon precursor. Advantageously, both of these starting materials are cheap and commercially available, and the synthesis can be easily scaled up. The mesopore size of CIM carbon can be tuned by the size of the colloidal silica particles, preferably ranging from about 2 to about 50 nm, more preferably between about 15 and 50 nm, depending on the source of colloidal silica. Due to its pore texture, CIM carbon can exhibit a higher capacitance than 3DOM carbon. In addition, the high purity carbon precursor for CIM carbon, i.e., the mesophase pitch, can introduce fewer redox-active surface functional groups. Pitch materials obtained from coal tar or petroleum products have mixed compositions and are difficult to purify. The type of mesophase pitch used as precursor for the preparation of CIM carbon is preferably a fully synthetic material, and is more preferably, prepared by condensation of an aromatic hydrocarbon which can provide exceptional purity and low oxygen content (Mochida et al. 1990). Unlike monolithic 3DOM carbon, CIM carbon can be prepared in powder form and can be made into thin films for mass production and fabrication. Examples 1 and 2 below describe one exemplary method for synthesizing CIM carbon and forming the CIM carbon interlayer. The CIM carbon can have mesopores with an average diameter between about 2 nm and about 50 nm. In an exemplary embodiment, the electrodes include CIM carbon with mesopores having an average diameter between about 15 and about 50 nm diameter.

The interlayer in the electrodes is generally a thin film of varying thickness. The thickness of the CIM carbon interlayer can be, for example, between about 0.5 µm and about 1000 µm. In one exemplary embodiment, the CIM carbon interlayer is between about 50 µm about 250 µm. Interlayer thickness can depend on the specific use and may also be outside of this range and all are within the scope of this invention.

Electrodes with CIM carbon with interconnected mesopores as the intermediate layer between a gold electrode and an ionophore-doped ISM can exhibit good Nernstian response with a slope of about 59.5 mV/decade in the range from about $10^{-5.2}$ to about $10^{-10}$ M when valinomycin is used as $K^+$ ionophore. Advantageously, intrinsic hydrophobic characteristics of CIM carbon prepared from mesophase pitch lead to outstanding performance of the sensors, with excellent resistance to the formation of a water layer and no interference caused by light, $O_2$, and $CO_2$. When a redox couple is introduced as an internal reference species, calibration-free SC-ISEs can be made with a standard deviation of $E°$ about 2.0 mV or lower, preferably as low as 0.7 mV or lower. Moreover, the interconnected mesopore structure of ISE membrane-infused CIM carbon facilitates both ion and electron conduction and provides a large interfacial area with good ion-to-electron transduction. Because of the large double-layer capacitance of CIM carbon, CIM carbon-based SC-ISEs exhibit excellent potential stability, as shown by chronopotentiometry and continuous long-term measurements.

Chronopotentiometry shows that the capacitance of the ISEs described herein can vary depending on the specific use. Capacitance of the ISEs, for example, can be between about 100 mF and about 0.01 mF. In some exemplary embodiments, the capacitance of the ISEs can be about 1.0 mF. Capacitance values outside of this range are also within the scope of this invention.

The long-term emf drift of the SC electrodes can vary. In some embodiments, the long-term emf drift can be about 100 µV/h or lower, preferably about 10 µV/h and more preferably about 2 µV/h or lower. In some exemplary embodiments, the long-term emf drift of SC-ISE can be about 1.3 µV/h or lower, making these electrodes very stable. In other exemplary embodiments, the long-term drift of the SS-reference electrode can be 1.7 µV/h or lower.

Benefiting from the aforementioned characteristics, CIM carbon-based electrodes exhibit excellent theoretical (Nernstian) response and potential stability. The CIM carbon based solid contact electrodes can be combined with a variety of redox buffers to enhance the potential stability. Redox buffers that can be used include any redox active pair of a reduced organic or organometallic complex along with the oxidized species that is formed by removal of one or more electrons from the reduced species, provided that both the reduced and the oxidized species are chemically stable in the ISM membrane. By having both the reduced and the oxidized species present, a redox buffer is created that helps to stabilize the interfacial potential. In an exemplary embodiment, when combined with a redox buffer layer provided by the tetrakis(pentafluorophenyl)borate (TPFPB$^-$) salts of cobalt(II) and cobalt(III) tris(4,4'-dinonyl-2,2'-bipyridyl) ([Co(C$_9$,C$_9$-bipy)$_3$]$^{2+/3+}$), SC-ISE electrodes can be fabricated, for example, with a standard deviation of E as low as 0.7 mV. In another exemplary embodiment, a SS-reference electrode can be fabricated, for example, with a standard deviation of E as low as 2.8 mV. For many applications these sensors can be substantially calibration-free or used without prior calibration.

The ISEs described herein also include an ISM disposed over and in contact with the CIM carbon interlayer. A variety of ISM's are known to be functional in electrochemical sensors and all are within the scope of this invention. Exemplary ISM's include membranes with selectivity for $H^+$, $Li^+$, $Na^+$, $K^+$, $Mg^{2+}$, $Ca^{2+}$, $Cu^{2+}$, $Ag^+$, $Zn^{2+}$, $Cd^{2+}$, $Hg^{2+}$, $Pb^{2+}$, $NH_4^+$, carbonate, bicarbonate, nitrate, nitrite, sulfide, chloride, iodide, and the like, as well as organic anions and cations such as heparin, protamine, and the like. Preferably, the ISM's are ionophore-doped. Exemplary ionophore doped ISMs includes $K^+$-ISMs doped with valinomycin, $H^+$-ISMs with pyridine or trialkylamine derivatives as ionophores, $Li^+$, $Na^+$, and $K^+$-ISMs with crown ether, calixarene, or oligoamide ionophores, and carbonate ISEs with trifluoroacetylphenone derivatives as ionophores as known in the art. The thickness of the ISMs can vary and is generally determined by the desired use. In some exemplary embodiments, ISM thickness can be between about 20 µm and about 500 µm. In some preferred embodiments the ISM thickness is about 100 µm. ISM thicknesses outside of this range are also within the scope of this invention.

In embodiments including SS-reference electrodes, the reference membrane is preferably a hydrophobic reference membrane attached to an electronically conducting solid contact, thus resembling the setup of an SC-ISE. The reference membranes are usually doped with ions that can leach into the samples on a slow but continuous basis so that the phase boundary potentials at the reference membrane/sample interfaces are sample-independent and defined by the interfacial distribution of the doping ions. Several ions can be doped into reference membranes, including polyions, ionic liquids, and lipophilic and hydrophilic salts. At the reference membrane/solid contact interface, the interfacial potential can be stabilized by employing various solid contacts that are also used in SC-ISEs as described herein. The SS-reference electrodes can have a high capacitive interface between the reference membrane and the solid contact and the solid contact can provide for a high potential stability. Advantageously, light, and oxygen do not significantly affect the SS-reference electrodes. $CO_2$ may affect the SS-reference electrodes in unbuffered solutions but does not affect them in buffered solutions. The measurement with a reference electrode using the CIM carbon may be calibration-free.

The solid contacts for SS-reference electrodes can also include conducting polymers, and nanostructured carbon materials, such as three-dimensionally ordered macroporous (3DOM) carbon, carbon nanotubes, and graphene.

The reference membranes are preferably doped, and more preferably doped with a hydrophobic redox couple. The reference membrane may also be doped with an ionic liquid. In an exemplary embodiment, the reference membranes are doped with the ionic liquid 1-methyl-3-octylimidazolium bis(trifluoromethylsulfonyl)imide ($[C_8min^+][C_1C_1N^-]$) to define the potential at the reference membrane/sample interface, as well as a hydrophobic redox buffer consisting of $[Co(C_9,C_9\text{-bipy})_3](TPFPB)_2$ and $[Co(C_9,C_9\text{-bipy})_3](TPFPB)_3$ to define the potential at the CIM carbon/reference membrane interface. Other suitable examples of redox couples include, for example, tetrakis(pentafluorophenyl)borate ($TPFPB^-$) salts of cobalt(II)tris(1,10-phenanthroline) and cobalt(III)tris(1,10-phenanthroline). Other ionic liquids and hydrophobic redox couples may be used and are within the scope of this invention. Alternative lipophilic anions to produce redox buffers with redox-active cations include tetraphenylborate and tetraphenylborate derivatives with one or multiple chemically inert substituents such as halide, alkyl, aryl, nitro, and ether groups. Alternative lipophilic anions include naphthalenesulfonic acid derivatives with one or multiple chemically inert substituents such as halide, alkyl, aryl, nitro, and ether groups. Alternative redox-active cations include lipophilic complexes of Co, Mn, or Os, with pyridine, bipyridyl, phenanthrene, or derivatives thereof with inert substituents. Alternative ionic liquids may contain imidazolium cations substituted with any type of alkyl group on their nitrogens. Alternative ionic liquids may contain sulfonimids substituted with any type of perfluoroalkyl group.

The membranes of the electrodes can be made from a variety of polymeric matrices. Suitable polymers for membranes useful in an electrode are known in the art and all are within the scope of this invention. The polymeric matrix can be, for example, polyvinyl chloride (PVC), polyurethane, silicone rubbers, polyvinyl butyral, polyacrylate, a perfluoropolymer and the like.

Benefiting from the high capacitance of the interface between the CIM carbon and the reference membrane, outstanding potential stability can be observed, with a potential drift as low as 1.7 µV/h over 110 h, making CIM carbon-based reference electrodes a very stable all SS-reference electrode. The CIM carbon-based reference electrodes can be compatible with miniaturized potentiometric systems and can also be integrated into disposable paper-based sensing devices, e.g. $Cl^-$ sensing devices, to replace the conventional Ag/AgCl reference electrodes, eliminating the reference electrolyte and the associated liquid junction potentials.

The SS-reference electrode including the CIM carbon interlayer generally has a low potential variability. For electrolytes with different charges and hydrophilicities, there is only a very small emf response of the SS reference electrode in the $10^{-7}$ M to $10^{-1}$ M concentration range, and preferably in an even wider range of $10^{-14}$ M to $10^{-1}$ M. The change in emf is preferably less than about 3.0 mV/decade, more preferably less than about 2.0 mV/decade and even more preferably less than about 1.0 mV/decade.

The standard deviation of measured $E°$ in SS-reference electrodes is preferably less than about 10 mV, more preferably less than about 5 mV, even more preferably less than about 3 mV. The potential drift of the SS-reference electrode is generally low. The potential drift of the SS-reference electrode is preferably less than about 3 µV/h and more preferably less than about 2 µV/h.

The present description also includes an electrochemical sensor system. The electrochemical sensor system components include SC-ISE as described herein with the CIM carbon interlayer. The electrochemical system can include a workstation and 2, 3 or 4 electrodes. At least one of the electrodes can be an SC-ISE. In some preferred embodiments, all of the electrodes in the system are SC-ISEs. The SC-ISEs of the system may not require calibration. The electrochemical sensor system may also include a reference electrode with a CIM carbon interlayer. The electrochemical sensor system components may also include a work station, power source, sample holder, computer and/or recorder with optionally a display. The recording device and/or computer can record and/or compute the amount or concentration of an analyte in a sample. The components of the electrochemical sensor systems may be integral within the system, i.e. housed together, or they may be separate components that can be electrically connected to form the electrochemical sensor systems.

Figure 1B:
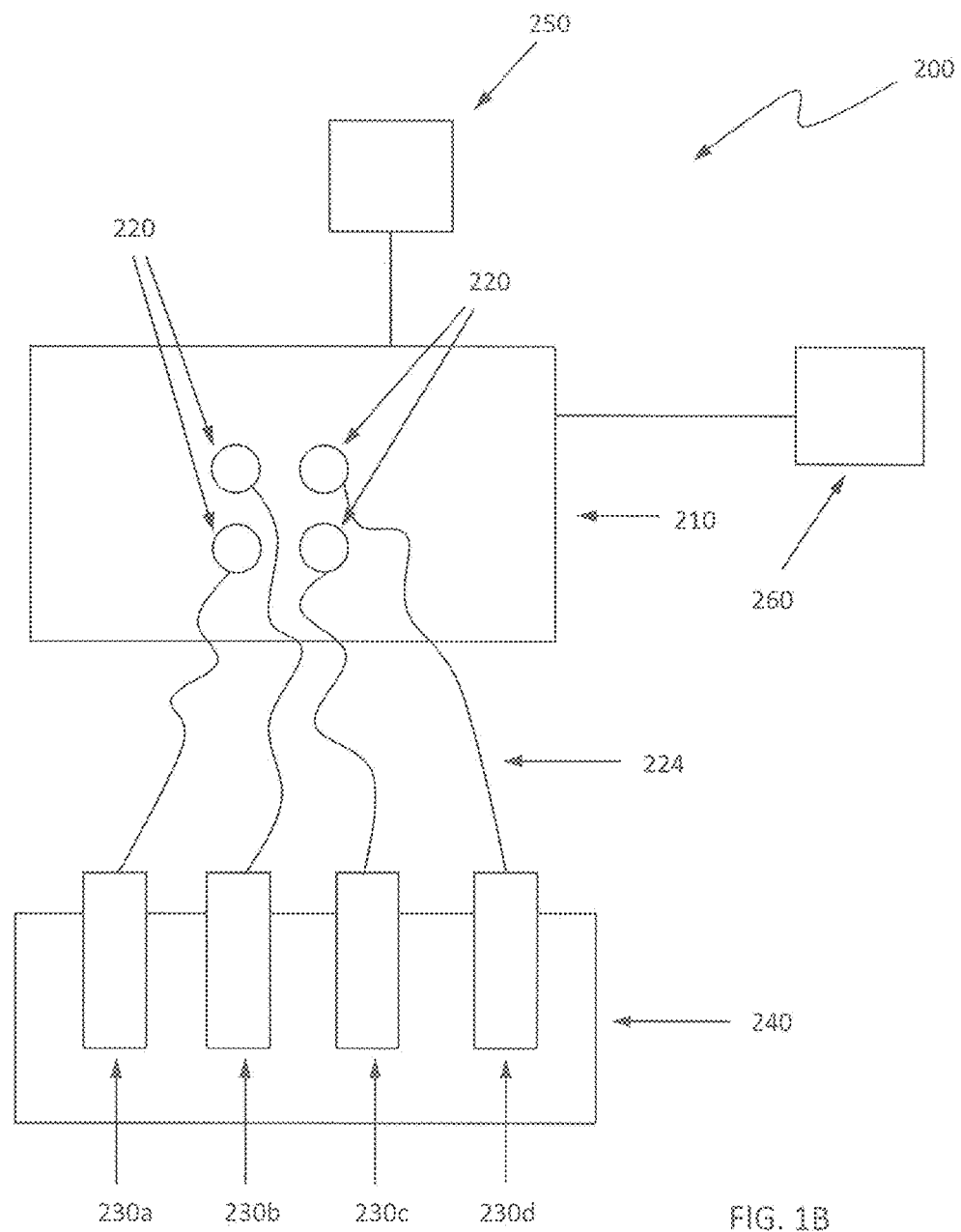
FIG. 1B is a schematic diagram of an electrochemical system of the present description.

FIG. 1B is a schematic of an exemplary electrochemical system 200. System 200 includes workstation 210 configured with openings 220 to receive connectors 224. Connectors 224 connect electrodes 230a, 230b, 230c and 230d to workstation 210. Electrodes 230a, 230b, 230c and 230d during use can be placed in sample holder 240 with a sample. Workstation 210 can be connected to power source 250. Workstation 210 may be optionally operably connected to computer 260.

The electrochemical sensor system may be configured to be, for example, a potentiometric sensor, an ion-sensitive field effect transistor, a voltammetric sensor, an amperometric sensor, a coulometric sensor or an impedance sensor. A general electrochemical measurement system can include, for example, an electrochemical workstation that can be connected to a plurality of electrodes. The electrochemical workstation may be connected to two, three, or four electrodes. All of the electrodes can be in contact with the sample. In one exemplary embodiment with a potentiometric system, a reference and sensing electrode are connected to the workstation, which is referred to as a potentiometer. In an embodiment with a voltammetric system, a reference, an auxiliary, and a sensing electrode are connected to the workstation. Impedance measurements can be performed with two, three or four electrodes. Other components known in the art may also be present and may also be part of the electrochemical system and all are within the scope of the present description.

The present description includes paper-based sensing devices. The paper-based devices can be disposable and may be potentiometric sensing devices. A variety of ions or analytes in samples can be detected in the paper-based devices as described above for the ion-selective electrodes including, for example, $H^+$, $Li^+$, $Na^+$, $K^+$, $Mg^{2+}$, $Ca^{2+}$, $Cu^{2+}$, $Ag^+$, $Zn^{2+}$, $Cd^{2+}$, $Hg^{2+}$, $Pb^{2+}$, $NH_4^+$, carbonate, bicarbonate, nitrate, nitrite, sulfide, chloride, iodide, and the like, as well as organic anions and cations such as heparin, protamine, and the like. The paper-based device can include a SS reference electrode and an ISE. The ISE can be stencil-printed Ag/AgCl electrode.

In an exemplary embodiment, a paper-based potentiometric sensing device is a $Cl^-$ sensing device. The miniaturized potentiometric $Cl^-$ sensing devices can be fabricated on paper. The paper-based sensing device includes a stencil-printed Ag/AgCl electrodes serving as the ISE and a SS reference electrode that includes the CIM carbon. The paper-based system may also include a SS reference electrode and a SC-ISE.

Figure 14:
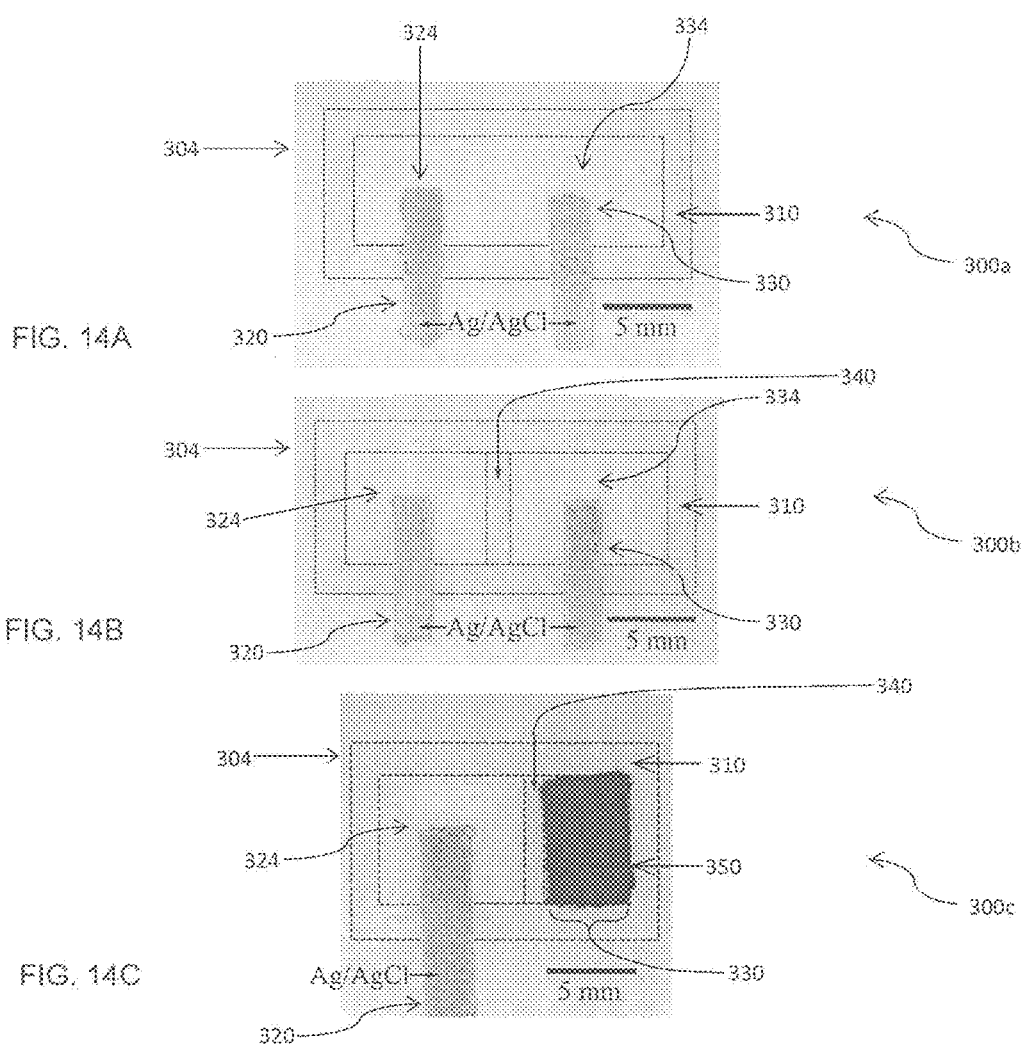
FIG. 14a, FIG. 14b and FIG. 14c are photographs of paper-based potentiometric $Cl^-$ sensing devices with different designs.

FIGS. 14a-c show three exemplary embodiments of paper-based sensing devices 300a, 300b and 300c. Devices 300a, 300b and 300c include paper 304 and barrier 310 to contain aqueous solutions. In one preferred embodiment, barrier 310 is a polyurethane barrier to contain aqueous solutions. Polyurethane can be used to form the hydrophobic barriers that define the microfluidic channels because it is inexpensive, readily commercially available, and can be inkjet-printed for mass fabrication. It can also avoid the melting process that is required to fabricate wax-printed paper devices. Other barriers that contain aqueous solutions may also be used. Examples of other barriers to contain aqueous solutions include wax.

Devices 300a-c also include stencil printed ISEs 320 and sample compartment 324. Device 300a includes reference electrode 330 and reference electrolyte solution 334. Device 300b includes reference electrode 330, reference electrolyte solution 334 and reference membrane 340. Device 300c includes reference electrode 330 with CIM carbon-reference membrane mixture 350 and reference membrane 340. Reference electrode 330 of device 300c includes a CIM carbon-reference membrane system (340 and 350) as shown if FIG. 14c to replace the conventional Ag/AgCl reference electrodes. Device 300b can also eliminate the liquid junction potentials at the sample/reference electrolyte interface because a reference membrane was integrated into the central zone of the device, as shown in FIG. 14b. The use of the CIM carbon-reference electrode can also enable elimination of the reference electrolyte. The paper-based device of FIG. 14c can eliminate the need for a reference electrolyte solution when using the device. In operation, a sample can be placed into compartment 324. In an exemplary embodiment, copper alligator clips can be used to connect the ISE and the CIM reference electrode to a potentiometer. Other methods of potentiometric determination may be used and all are within the scope of this invention.

Figure 17:
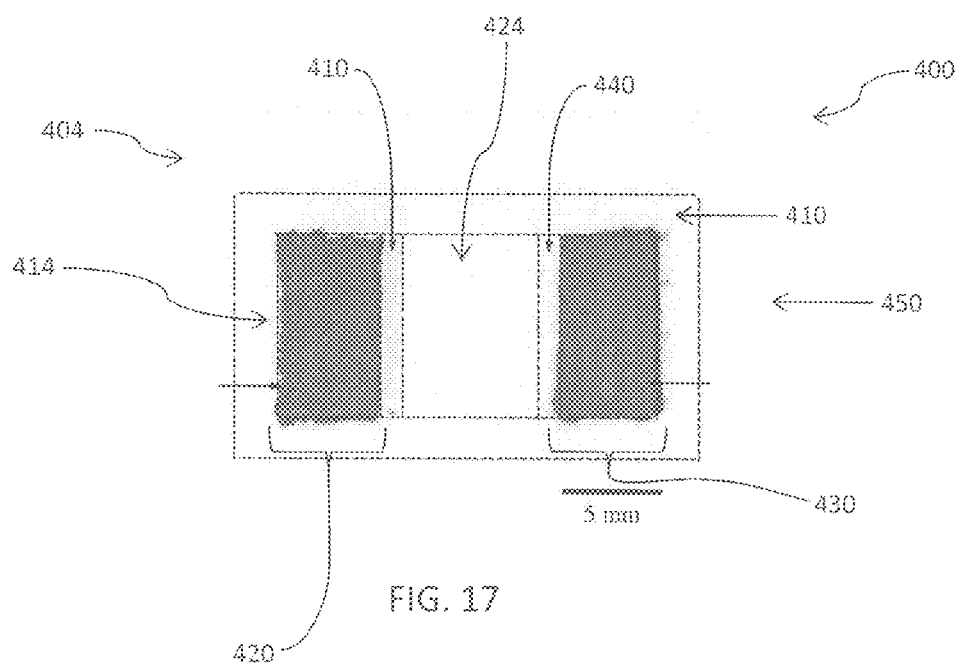
FIG. 17 is a photograph of paper-based potentiometric sensing device containing a CIM carbon-based SC-ISE and a CIM-carbon based SS-reference electrode.

FIG. 17 shows another exemplary embodiment of a paper-based sensing devices 400. Device 400 includes paper 404 and barrier 410 to contain aqueous solutions. In one preferred embodiment, barrier 410 is a polyurethane barrier to contain aqueous solutions. Device 400 includes SC-ISE 420 and SS-reference electrode 430. SC-ISE 420 includes CIM carbon-ISE membrane mixture 414 with ISM 410. SS-reference electrode 430 includes CIM carbon-reference membrane mixture 450 with reference membrane 440. Device 400 includes sample compartment 424. In operation, a sample can be placed into compartment 424. In an exemplary embodiment, copper alligator clips can be used to connect the CIM-ISE and the CIM reference electrode to a potentiometer.

The paper-based devices generally exhibits a reproducible Nernstian response. In one exemplary embodiment in a $Cl^-$ sensing device, the Nernstian response has a slope of about −60 mV/decade.

Sample size to be analyzed in the paper-device device can vary. The size of the sample can vary, for example, between about 1 µL and about 200 µL. Sample sizes can be, for example, between about 5 µL and about 100 µL. In one exemplary embodiment, sample sizes as small as of about 10 µL can be analyzed.

The present description includes a method for forming the CIM carbon interlayer in the fabrication of the SS-electrodes described herein. The electrodes can be a SC-ISE electrode or a SS-reference electrode. The method can include using CIM carbon synthesized from synthetic material such as aromatic hydrocarbons. The synthetic material can be, for example, mesophase pitch. Methods for synthesizing CIM carbon are known in the art and can be, for example, the method described in U.S. Pat. No. 7,666,380 to Jaroniec and incorporated herein by reference. The synthetic material could also be any other type of aromatic hydrocarbon that does not evaporate above roughly 500° C. but softens above roughly 200° C. so as to allow the template to penetrate the synthetic material. Mesophase pitch can be ground and dispersed in a solution, for example, as described below in Example 1. The mesophase pitch powder can be treated with colloidal materials such as colloidal silica. Other colloidal materials may also be used and these colloidal materials are generally small spherical particles with diameter that correspond to the desired size of the mesopores in the CIM carbon.

The method includes using CIM carbon as the interlayer between the solid electron conductor and the membrane. The membrane can be an ISM or a reference membrane. The method includes forming a thin film with the CIM carbon over the solid electron conductor. The CIM carbon powder can be formed into a suspension and drop cast over the solid electron conductor such as a gold disk to form thin films.

The thickness of the film can vary and can be, for example, between about 0.5 μm and about 1000 μm, preferably between about 50 μm and about 250 μm.

The method also includes forming or placing a membrane over the interlayer. In an exemplary embodiment, an ISM is placed over the interlayer. Preferably, an ionophore-doped membrane is formed over the interlayer. An exemplary ISM is a valinomycin-doped K membrane. Other ionophore-doped membranes as described above are also within the scope of this invention. The ISM can be of varying thickness and preferably between about 20 μm and 500 μm and more preferably about 100 μm. To prevent delamination of the interlayer and the ISM, the electrode may be mounted into a cylindrical body and/or other appropriate housing to gently press the ISM and interlayer onto the conductor of the electrode.

In another exemplary embodiment, a reference membrane is placed over the CIM-carbon interlayer. Preferably, the reference membrane formed over the interlayer is doped with a moderately hydrophilic ionic liquid and a hydrophobic redox couple. A variety of hydrophilic ionic liquids and hydrophobic redox couples can be used. In one exemplary embodiment, the ionic hydrophilic liquid [$C_8$min+][$C_1C_1N^-$] and hydrophobic redox couple [$Co(C_9,C_9$-bipy$)_3$]$^{2+/3+}$ is used. Other membranes as described above are also within the scope of this invention. The reference membrane can be of varying thickness and preferably between about 20 μm and 500 μm and more preferably about 100 μm. To prevent delamination of the interlayer and the reference membrane, the electrode may be mounted into a cylindrical body and/or other appropriate housing to gently press the reference membrane and interlayer onto the conductor of the electrode.

The present description includes a method for measuring analytes in a sample. The analytes are generally ions in a sample. The ions may be in natural substances or synthetic substances. The samples can be clinical samples, environmental samples, industrial samples, forensic samples, agricultural samples, and the like. Clinical samples can include samples generated in hospitals, clinics, in point-of-care scenarios such as home or other settings. Clinical samples can be from healthy individuals or individuals with medical issues. The samples may be liquid or gas samples. If the sample is a gas, the electrochemical sensor may be or may not be separated from the sample by a gas-permeable membrane.

The method includes placing a sample in a system so that it will contact the ISE. The system may include one or more SC electrodes. In some embodiments, the system includes a SC-ISE. The electrode(s) with the CIM carbon interlayer can be used in an electrochemical sensor to determine the concentration or amount of the analyte in the sample. The amount and/or concentration of the sample can be measured using a variety of techniques and characteristics. The samples may be analyzed using potentiometric, voltammetric, amperometric, coulometric or impedance methods known in the art. Other methods compatible with electrochemical sensors may also be used and are within the scope of this invention. The results may then be correlated with known concentrations of the analytes to determine the quantity or concentration of the analyte in the sample.

The present description also relates to a method of measuring an analyte in a system that includes a solid-contact reference electrode wherein the solid-contact reference electrode comprises mesoporous carbon interlayer, preferably a CIM carbon interlayer. A solid-contact reference electrode with a polymeric reference membrane can be prepared in a manner similar to those of ion-selective electrodes described herein with an ion-selective ionophore-doped, polymeric membrane. A solid contact reference electrode with an interlayer of mesoporous carbon includes a solid electron conductor, an interlayer comprising mesoporous carbon, and a polymeric reference membrane including a polymer and, an ionic liquid, and with/without a redox couple. A sample can be placed that will come into contact with an ISE that is also in the system. The samples may be analyzed using potentiometric, voltammetric, amperometric, coulometric or impedance methods known in the art. Other methods compatible with electrochemical sensors may also be used and are within the scope of this invention. The results may then be correlated with known concentrations of the analytes to determine the quantity or concentration of the analyte in the sample.

The present description also relates to a method of measuring an analyte in a paper-based sensing device. The paper-based device can be a disposable, potentiometric sensing device. The method includes applying a sample to the area around the ISE. The size of the sample can vary. In some embodiments, the sample can be, for example, between about 5 μL and about 200 μL. The sample can be placed so that it can come into contact with the ISE. The ISE can be, for example, stencil-printed onto the paper-based device. The paper-based device can include a SS reference electrode with the CIM carbon. The method includes measuring the electrode potentials with a potentiometer and correlating the results of the potentiometer readings to determine the analyte quantity or concentration in a sample. The potentiometer readings, for example, may be correlated to readings obtained from known concentration of analytes in standard samples to determine the analyte concentration in a sample.

EXAMPLES

Example 1

CIM Carbon Synthesis and Fabrication of Electrode

Materials. Reagents were obtained from the following sources: mesophase pitch from Mitsubishi Gas Chemicals (Tokyo, Japan), Ludox AS-40 colloidal silica, sodium ethoxide solution (21 wt % in ethanol), bromocresol green/methyl red (mixed indicator solution in methanol), tetraethylammonium tetrafluoroborate (TEABF$_4$), and valinomycin from Sigma-Aldrich (St. Louis, Mo.), o-nitrophenyl octyl ether (o-NPOE), and high molecular weight poly(vinyl chloride) (PVC) from Fluka (Buchs, Switzerland), sodium tetrakis[3,5-bis-(trifluoromethyl)phenyl]borate (NaTFPB) from Dojindo (Kumamoto, Japan), and lithium tetrakis(pentafluorophenyl)borate (LiTPFPB) ethyl etherate from Boulder Scientific (Boulder, Colo.). All chemicals were used as received without further purification. Deionized water was purified to a resistivity of 18.2 MΩ/cm with a Milli-Q PLUS reagent-grade water system (Millipore, Bedford, Mass.). The redox couple consisting of [$Co(C_9,C_9$-bipy$)_3$](TPFPB)$_2$ and [$Co(C_9,C_9$-bipy$)_3$](TPFPB)$_3$ was synthesized as reported (Zou et al. 2014).

CIM Carbon Synthesis.

The CIM carbon was synthesized using a modification of a previously reported route (Li et al. 2001). A mass of 5 g of mesophase pitch was manually ground and dispersed in 100 mL of an ethanol/water mixture (~60:40 volume ratio) at 50° C. Under vigorous stirring, 100 mL of Ludox AS-40 colloidal silica suspension was added gradually into the flask, and the resulting mixture was stirred overnight at 50° C. The resulting mixture was transferred to an open plastic beaker, stirred, and kept at 50° C. overnight to allow solvent evaporation. The obtained pitch-silica composites were then transferred into a porcelain combustion boat and heated under a $N_2$ flow (0.5 µL/min) with a heating ramp of 5° C./min to 400° C., at which temperature it was kept for 2 h. The subsequent carbonization at 900° C. for 2 h in a $N_2$ atmosphere converted the pitch-silica composites to carbon-silica composites. To remove the silica spheres, the carbon-silica composites were then soaked in 6 M KOH aqueous solution and kept for 48 h at 180° C. in a Teflon-lined steel autoclave. The obtained CIM carbon was filtered and washed with copious amounts of water until the pH was 7. Before use, the CIM carbon was pyrolyzed under a 5% $H_2$, 95% $N_2$ flow (0.6 µL/min) at 900° C. for 5 h to reduce absorbed moisture and functional groups on the carbon surface.

Electrode Fabrication.

The 2 mm diameter gold disk electrodes (gold disks embedded into a cylindrical plastic body, CH Instruments, Austin, Tex.) were polished over polishing cloths with aqueous dispersions of alumina (0.3 and 0.05 µm, Buehler, Lake Bluff, Ill.). They were cleaned by ultrasonication in water and ethanol, and dried with a flow of argon. CIM carbon powder was manually ground for 5 min. The CIM carbon suspension was prepared by ultrasonicating 47.5 mg of CIM carbon and 2.5 mg of PVC as binder in 1 mL of freshly distilled tetrahydrofuran (THF) for 30 min. An amount of 30 µL of the CIM carbon suspension was dropcast onto gold electrodes and left to dry, forming CIM carbon films with a thickness of approximately 200 µm.

Precursor solutions for valinomycin-doped $K^+$-ISMs were prepared by dissolving in 1 mL of freshly distilled THF 66 mg of PVC as polymer matrix, 132 mg of o-NPOE as plasticizer, 2.0 mg of valinomycin as ionophore, and 1.2 mg of NaTFPB (75 mol % with respect to the ionophore) to provide for ionic sites. Solutions for $K^+$-ISMs doped with the redox couple were prepared by dissolving in 1 mL freshly distilled THF 66 mg of PVC, 132 mg of o-NPOE, 2.0 mg of valinomycin, 0.6 mg of LiTPFPB ethyl etherate (46 mol % with respect to the ionophore) to provide for anionic sites, and 1.4 mmol/kg each of $[Co(C_9,C_9\text{-bipy})_3](TPFPB)_2$ and $[Co(C_9,C_9\text{-bipy})_3](TPFPB)_3$.

To form ISMs with a thickness of approximately 100 µm, two portions of one of the above solutions (20 µL, followed by 30 µL) were dropcast onto the CIM carbon layer on a gold disk electrode. As a precaution to avoid the possible delamination of the ISMs and CIM carbon films from the gold electrodes, the coated electrodes were mounted into cylindrical bodies custom-made from the Dupont™ Delrin® acetal resin. A screw cap at the opposite end of the electrode allowed to gently press the ISM with the CIM carbon film onto the electrode (see FIGS. 1A and 7). (Use of gold disk electrodes embedded into or printed onto a PVC compatible polymer, rather than the commercial gold disk electrodes as used here, would make the cylindrical bodies unnecessary.) Prior to measurements, the electrodes with the redox couple were conditioned in 1.0 mM KCl solution for 1 h, and those without the redox couple for 24 h. The short conditioning time of the electrode membranes containing the redox couple minimized the loss of redox couple species by leaching into the aqueous solution (Zou et al. 2014).

Structure of CIM Carbon.

Figure 8:
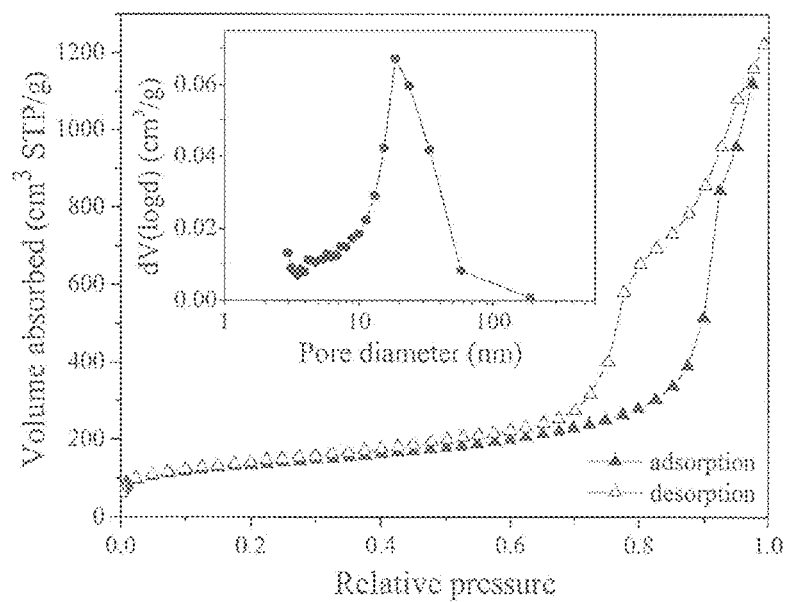
FIG. 8 is a graph showing the nitrogen sorption isotherm of CIM carbon and the corresponding BJH pore size distribution is shown in the inset.

The CIM carbon prepared in this work consisted of remarkably uniform mesopores of about 24 nm (FIG. 8) due to the monodispersity of the colloidal silica particles that were used to template the pores (Li et al. 2001). As the TEM image in FIG. 1A shows, these mesopores are highly interconnected but randomly distributed, which is different from the periodic nature of 3DOM carbon. After manual grinding for 5 min, CIM carbon particles have irregular shapes with average sizes of approximately 15 µm. When used in a SC-ISE, these particles are bound together by the PVC binder as well as the plasticized ISM.

Purity and Surface Functionality of CIM Carbon.

CIM carbon exhibits higher purity and fewer surface functional groups than 3DOM carbon because its carbon precursor, the mesophase pitch is a polyaromatic resin produced by catalytic synthesis from naphthalene, comprising only carbon and hydrogen (Mochida et al. 1990). In comparison, the resorcinol-formaldehyde precursor of 3DOM carbon contains a considerable amount of oxygen, which can introduce oxygen-based impurities. As shown in Table 1, the oxygen content of CIM carbon is 0.43 wt %, i.e., 1.7 wt % lower than that of 3DOM carbon synthesized from resorcinol-formaldehyde. The surface functionality of CIM carbon was characterized by acid-base titrations with four different bases, as previously reported (Fierke et al. 2010; Boem et al. 1964). In contrast to 3DOM carbon (see Table 2), no phenol functional groups are detected, and the ketone content is cut in half. The residual trace amount of oxygen in CIM carbon may arise from the KOH hydrothermal treatment used to remove the silica template as well as from small amounts of unremoved silica.

TABLE 1

Elemental Analysis Data for CIM Carbon and 3DOM Carbon[a]

|  | C (wt %) | H (wt %) | O (wt %) | N (wt %) |
| --- | --- | --- | --- | --- |
| CIM carbon | 96.02 | 0.46 | 0.43 | 0.00 |
| 3DOM carbon | 92.95 | 0.27 | 2.13 | 0.00 |

[a]All elemental analysis values are ±0.3% according to Atlantic Microlab.

TABLE 2

Concentration of Functional Groups on the Surface of CIM Carbon and 3DOM Carbon

|  | ketone (mmol/g) | phenol (mmol/g) | lactone and lactol (mmol/g) | carboxylic acid[a] (mmol/g) |
| --- | --- | --- | --- | --- |
| CIM carbon | 0.17 | 0.00 | 0.00 | 0.00 |
| 3DOM carbon | 0.34 | 0.27 | 0.00 | 0.00 |

[a]The titration method cannot distinguish between carboxylic acid and anhydride functional groups, which may also be present.

Example 2

CIM Carbon Characterization

Acid-base titrations to determine surface functional groups were performed according to a previously reported procedure (Fierke et al. 2010; Boem et al. 1964). C, H, N elemental analyses were performed by Atlantic Microlab (Norcross, Ga.). Transmission electron microscopy (TEM) was carried out with a Technai T12 microscope (FEI, Hillsboro, Oreg.) operating at 120 kV with emission currents ranging from 7 to 12 µA. Nitrogen-sorption measurements were performed on an Autosorb iQ$_2$ gas sorption analyzer (Quantachrome, Boynton Beach, Fla.), with samples outgassed at 1 mTorr at 200° C. for 12 h before measurements. Specific surface areas were calculated by the Brunauer-Emmett-Teller (BET) method, and the pore sizes and volumes were estimated from the pore size distribution curves obtained from the adsorption branches of the isotherms using the Barrett-Joyner-Halenda (BJH) method.

Potentiometric Measurements.

Electrode potentials were measured with an EMF 16 potentiometer (input impedance 10 TΩ) controlled by EMF Suite 1.03 software (Lawson Labs, Malvern, Pa.). A double-junction type external reference electrode (DX200, Mettler Toledo, Switzerland; 3.0 M KCl saturated with AgCl as inner filling solution and 1.0 M LiOAc as bridge electrolyte) was used. Activity coefficients were calculated according to a two-parameter Debye-Hückel approximation, and all emf values were corrected for liquid-junction potentials with the Henderson equation (Meir 1982; Morf 1981).

Capacitance Measurements.

A three-electrode setup was used for measurements of the capacitance of CIM carbon. A gold electrode with a CIM carbon film was used as the working electrode, a Pt wire as the counter electrode, and an Ag wire in AgNO$_3$/acetonitrile as a nonaqueous reference electrode. To ensure complete wetting of CIM carbon, 0.1 M TEABF$_4$ in propylene carbonate was used as the nonaqueous electrolyte. The electrolyte solution was purged with argon for 15 min prior to each measurement.

For cyclic voltammetry experiments, a potential window of 0.6 V centered at 0.0 V with a scan rate of 0.5 mV/s was used. The capacitance was calculated by averaging the absolute value of the two current values at 0.0 V. This average current was then divided by the scan rate and the mass of the CIM carbon to give a specific capacitance value in F/g.

Electrochemical impedance spectroscopy (EIS) experiments were carried out on a Solartron 1255B frequency response analyzer with an SI 1287 electrochemical interface (Farnborough, Hampshire, U.K.) controlled by ZPlot software, and the data was fit using ZView software (Scribner Associates, Southern Pines, N.C.). The frequency range was 1 MHz to 0.01 Hz, with an ac amplitude of 10 mV versus the open circuit potential.

For chronopotentiometry experiments, a constant current of 0.1 mA was applied to the working electrode until an upper potential limit of 1.0 V was reached, at which time an equal but opposite current was applied to discharge the device until a lower potential limit of 0.0 V was reached. The specific capacitance in F/g was calculated by dividing the applied current by the mass of the CIM carbon and by the slope of the discharge curve in a potential versus time graph.

For chronopotentiometry measurements of the CIM carbon-based ISEs, an aqueous electrolyte of 1 mM KCl solution was used with the ISE as the working electrode, an aqueous double-junction Ag/AgCl (with a 1.0 M LiOAc bridge electrolyte and AgCl-saturated 3.0 M KCl inner reference electrolyte) as the reference electrode, and a Pt wire as the counter electrode. A constant current of +1 nA was applied to the ISE for 60 s, followed by a reverse current of the same magnitude for the same length of time (Bobacka 1999). The capacitance of the electrode was calculated by using the constant current divided by slope of the discharge curve in a potential versus time graph.

Capacitance of CIM Carbon.

Mesoporous carbon materials are well known for their high double-layer capacitance due to their large surface areas and highly accessible mesopores (Nishihara et al. 2012). In this study, three electrochemical techniques, i.e., cyclic voltammetry (CV), chronopotentiometry, and electrochemical impedance spectroscopy (EIS) were used to determine the specific capacitance of the CIM carbon. For all the measurements, a gold electrode with a CIM carbon film was used as the working electrode, with 0.1 M TEABF$_4$ in propylene carbonate as the electrolyte solution that effectively wets CIM carbon.

Figure 2A:
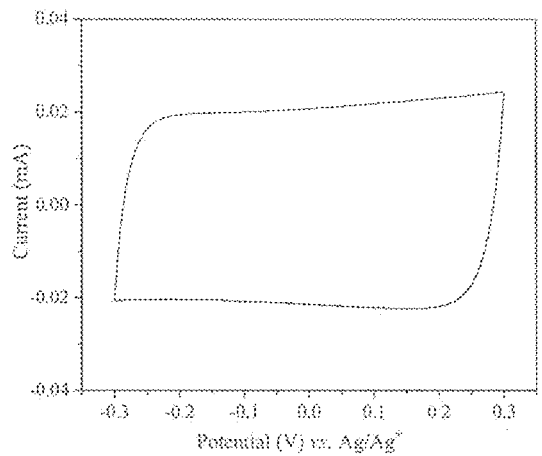
FIG. 2A-2C are graphs of capacitance measurements of a gold/CIM carbon electrode using 0.1 M tetraethylammonium tetrafluoroborate as the nonaqueous electrolyte.
Figure 2B:
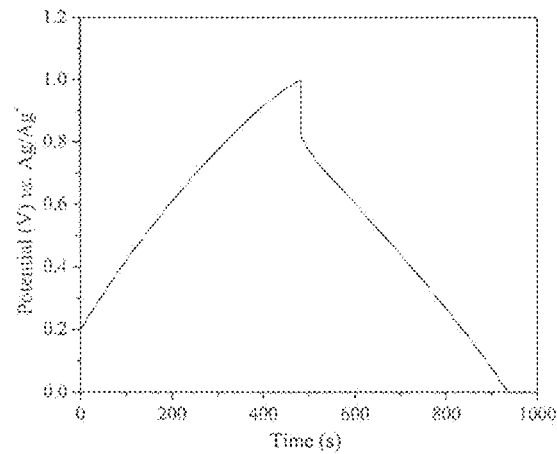
Figure 2C:
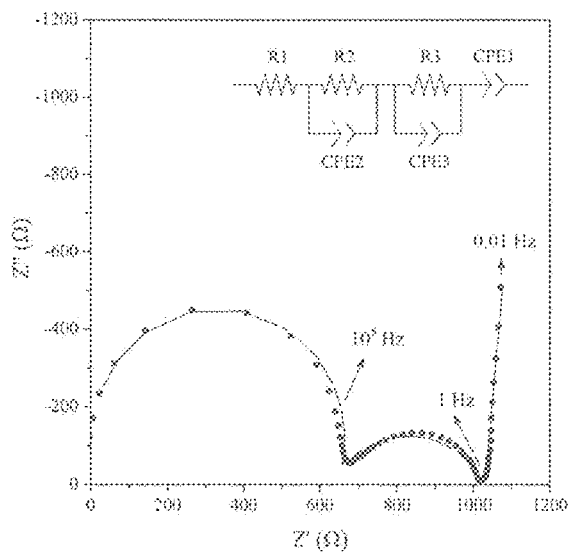

In the CV measurement obtained with a scan rate of 0.5 mV/s, a symmetrical curve without Faradaic currents, typical for capacitive behavior, is observed (FIG. 2A). The absence of Faradaic currents demonstrates the low amount of redox-active surface functional groups on the CIM carbon. For chronopotentiometry, a constant current of +0.1 mA was applied to the working electrode until the potential reached +1.0 V, and then a current of −0.1 mA was applied until the potential reached 0.0 V. Except for the immediate voltage drop after current reversal, the chronopotentiogram appears symmetrical with respect to charging and discharging (FIG. 2B). For the EIS data (FIG. 2C), the capacitance of CIM carbon can be represented by the impedance of the electrode at low frequencies ranging from 1 to 0.01 Hz. This data can be fitted with a constant phase element (CPE1 in FIG. 2C) with a capacitance of 27 mF and a phase value of 0.94, representing capacitive behavior. The specific capacitance of CIM carbon is obtained by dividing the absolute capacitance of the working electrode by the mass of CIM carbon. Those values are summarized and compared with the corresponding values for 3DOM carbon in Table 3. It is very likely that the different values determined with these electrochemical techniques are affected by the different magnitudes of current passing through the working electrode, which can affect the rate of ion transport across the interconnected mesopores of CIM carbon (Vu et al. 2013).

TABLE 3

Specific Capacitance of CIM and 3DOM Carbon as Measured by Different Methods

|  | CV[a] (F/g) | chrono-potentiometry[b] (F/g) | EIS (F/g) |
|---|---|---|---|
| CIM carbon | 31.3 | 40.7 | 20.5 |
| 3DOM carbon | 3.9 | 2.3 | 1.8 |

[a]Scan rate 0.5 mV/s.
[b]Current 0.1 mA.

Due to the occurrence of redox reactions in the CV and chronopotentiometry experiments for 3DOM carbon, specific capacitance values determined by EIS are more suitable for comparison (Fierke et al. 2010). This data shows that CIM carbon has a specific capacitance of 20.5 F/g, which is 11 times higher than that for 3DOM carbon. The large capacitance of CIM carbon is due to its interconnected mesopores with average diameters of about 24 nm that are accessible to the electrolyte, whereas less accessible micropores 1.8 nm in average diameter contribute to most of the surface area of 3DOM carbon (see Table 4). From nitrogen-sorption data (FIG. 8), the mesopore surface area of CIM carbon was determined to be 321 m$^2$/g, which is nearly 13 times that of 3DOM carbon. This ratio is in good agreement with the observed specific capacitance values for these two carbon materials.

TABLE 4

Textural Data of CIM Carbon and 3DOM Carbon

| | BET surface area (m²/g) | mesopore surface area (m²/g) | micropore surface area (m²/g) | mesopore volume (cm³/g) | micropore volume (cm³/g) | average pore diameter (nm) |
|---|---|---|---|---|---|---|
| CIM carbon | 442 | 321 | 117 | 1.65 | 0.07 | 23.7 |
| 3DOM carbon | 247 | 25 | 192 | 0.03 | 0.09 | 1.8 |

Ionic Response.

Figure 3:
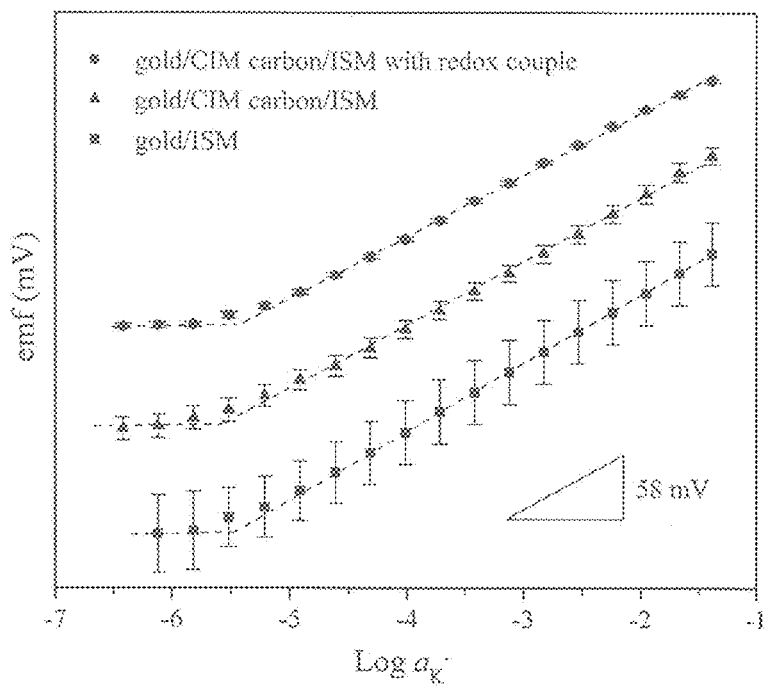
FIG. 3 is a graph of potentiometric $K^+$ response curves of SC-ISEs with different electrode configurations, i.e., a gold/CIM carbon/ISM with redox couple, a gold/CIM carbon/ISM, and a gold/ISM electrode. For clarity, response curves have been shifted vertically.

The ionic response of the CIM carbon-based SC-ISEs was measured by insertion of the electrodes along with a reference electrode into a 0.1 M KCl solution, followed by successive dilution of the sample and continuous monitoring of the emf. For comparison, three different electrode assemblies were used, i.e., a gold electrode with an ISM (gold/ISM), a gold electrode with a CIM carbon intermediate layer and an ISM (gold/CIM carbon/ISM), and a gold electrode with a CIM carbon layer and an ISM doped with the redox couple of $[Co(dibpy)_3](TPFPB)_2$ and $[Co(dibpy)_3](TPFPB)_3$ (gold/CIM carbon/ISM with redox couple). The corresponding calibration curves and other potentiometric $K^+$ response characteristics of these electrodes are shown in FIG. 3 and summarized in Table 5.

TABLE 5

Potentiometric $K^+$ Responses of Different Electrode Assemblies[a]

| substrate | slope (mV/decade) | E° (mV) | detection limit (M) | linear range (M) |
|---|---|---|---|---|
| gold/CIM carbon/ISM with redox couple | 57.3 ± 0.5 | 237.5 ± 0.7 | $10^{-5.4}$ | $10^{-5.0}$–$10^{-1.0}$ |
| gold/CIM carbon/ISM | 59.5 ± 0.6 | 58.8 ± 7.3 | $10^{-5.6}$ | $10^{-5.2}$–$10^{-1.0}$ |
| gold/ISM | 64.0 ± 1.4 | 466.6 ± 32.2 | $10^{-5.5}$ | $10^{-5.2}$–$10^{-1.0}$ |

[a]Average data and standard deviations are based on 6 electrodes. E° values refer to the potentials of the ISE cell as obtained by extrapolation of the linear section of the emf response to the $K^+$ activity of 1.0M.

Since there is no ion- and electron-conducting intermediate layer for the gold/ISM interface, the corresponding electrodes behaved quite poorly, as expected for coated wire electrodes. The reproducibility of the emf of these electrodes can be represented by the standard deviation of E°, which is as large as 32.2 mV due to the ill-defined interfacial potential. The slightly larger than Nernstian slope of 64.0 mV/decade is likely an artifact from the instability of E°. When CIM carbon is used as an intermediate layer between the gold electrode and the ISM, a Nernstian response with a slope of 59.5 mV/decade in the range from $10^{-5.2}$ to $10^{-1.0}$ M is observed. This response is consistent with a high stability of the interfacial potential of the solid contact and can be attributed to the ability of the CIM carbon to combine ionic and electronic conduction when the interconnected mesopores are filled with the ionophore-doped solvent polymeric sensing phase. The detection limit of these sensors is $10^{-5.6}$ M, and might be further improved by using reagents of higher purity and more dilute conditioning and starting solutions (Lai et al. 2009). Since no internal reference is present, the standard deviation of E° of these electrodes is 7.3 mV. The best results were obtained after the introduction of the redox couple as an internal reference standard since the interfacial potential between the CIM carbon and the ISM is well controlled by the redox couple (Zou et al. 2014; Zou et al. 2013). With a standard deviation of E° as low as 0.7 mV, these SC-ISEs may be used for some applications without calibration. We assume that the low amount of redox active impurities on the surface of CIM carbon is of particular importance for the proper functioning of the redox couple so that the interfacial potential between the CIM carbon and the ISM is controlled by the redox couple rather than redox active impurities.

Water Layer Test.

The formation of an unintentional thin water layer between the ISM and the solid contact is a common problem for SC-ISEs when these electrodes are exposed to aqueous solutions for long periods of time. The presence of this water layer can be tested with a method previously reported and is indicated by a positive potential drift when changing from a primary cation solution to a solution of a (discriminated) interfering cation, and a negative potential drift when changing back to the primary cation solution (Fibbioli et al. 2000).

Figure 4:
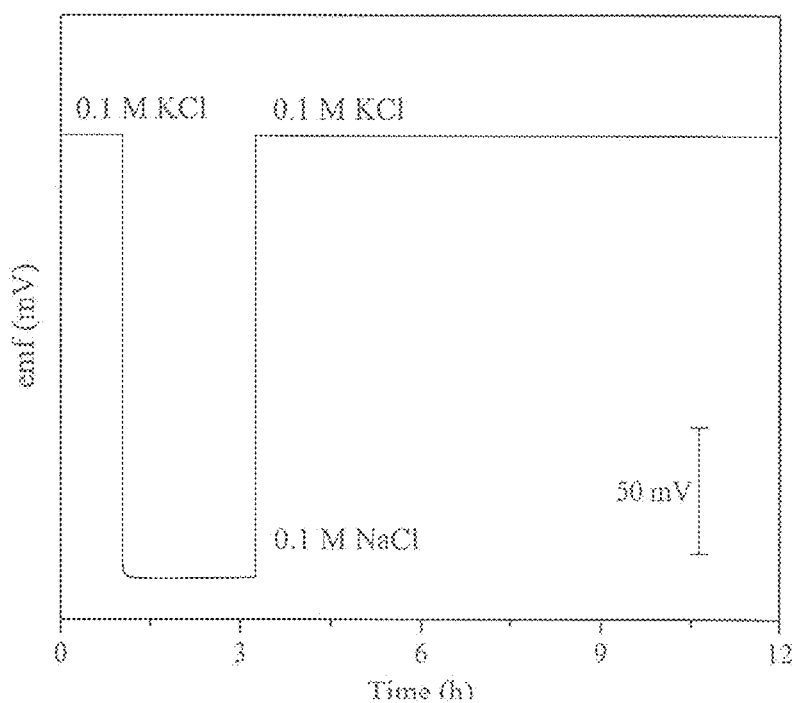
FIG. 4 is a graph of a water layer test for a gold/CIM carbon/ISM electrode. The electrode was immersed in a 0.1 M KCl solution for 24 h prior to the measurement. At t=1.03 h, the 0.1 M KCl solution was changed to a 0.1 M NaCl solution, and at t=3.25 h, the 0.1 M NaCl solution was changed back to a 0.1 M KCl solution.

In this experiment, the gold/CIM carbon/ISM electrodes were initially conditioned in a 0.1 M KCl solution for 24 h. At t=1.03 h, the 0.1 M KCl solution was replaced by a 0.1 M NaCl solution, and an immediate potential drop of 176 mV was observed, confirming a high selectivity for $K^+$ over $Na^+$. At t=3.23 h, the return to the 0.1 M KCl solution resulted in an immediate potential increase back to the original value (FIG. 4). During these processes, no potential drift was observed, indicating that no water layer had formed in the CIM carbon-based SC-ISEs. The absence of a water layer can be attributed to the highly hydrophobic surface of CIM carbon.

Effects of Light, Oxygen, and Carbon Dioxide.

Light, $O_2$, and $CO_2$ have been reported to cause interference for several SC-ISEs, especially for SC-ISEs with an interlayer of a conducting polymer (Vazquez et al. 2002). A SC-ISE can be photosensitive if the solid contact is an organic semiconductor with a suitable band gap. In addition, $O_2$ and $CO_2$ can diffuse across the ISM to reach the solid contact and cause interference. Specifically, $O_2$ can affect the phase boundary potential by forming an irreversible $O_2$ half-cell when redox active species are present, and $CO_2$ can alter the local pH when a water layer exists between the solid contact and the ISM (Lindner et al. 2009; Cattrall et al. 1975).

Figure 5:
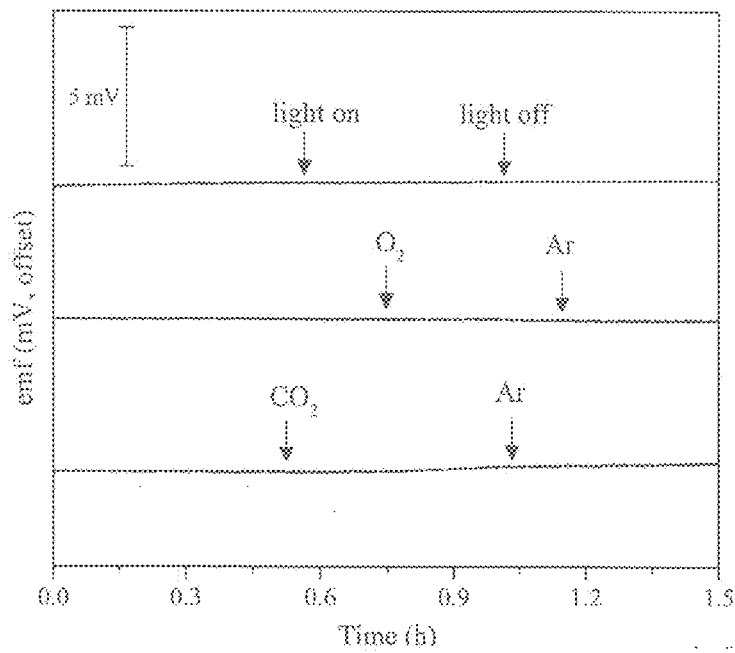
FIG. 5 is a graph showing the effects of light (top), $O_2$ (middle), and $CO_2$ (bottom) on the potential stability of gold/CIM carbon/ISM electrodes immersed in 1 mM KCl solution. For clarity, the emf responses of these electrodes have been shifted vertically.

In this study, the effect of light on the CIM carbon-based SC-ISEs was investigated by continuously recording the emf of gold/CIM carbon/ISM electrodes in a 1 mM KCl solution while turning on/off the ambient light. Effects of $O_2$ or $CO_2$ were tested by bubbling these gases through the solution, followed by purging with Ar to remove $O_2$ or $CO_2$. As illustrated in FIG. 5, when the sensors were exposed to light, $O_2$, or $CO_2$, no significant effect was recorded. The excellent resistance to these interferents relies on the low extent of surface functionality and the high hydrophobicity of the surface of CIM carbon.

Potential Stability.

Figure 6:
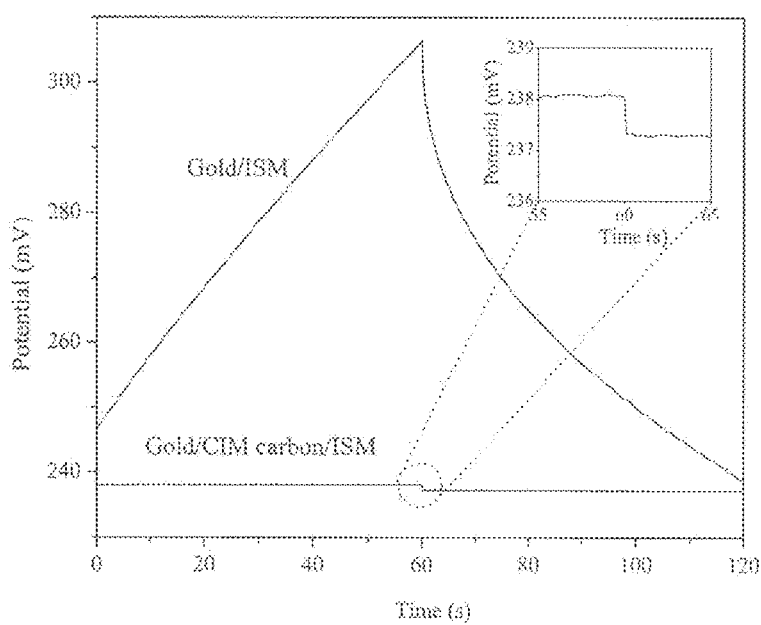
FIG. 6 is a graph of potential stability of gold/ISM (top) and gold/CIM carbon/ISM (bottom) electrodes under constant currents of +1 nA in 1 mM KCl solution. An expanded view showing the Ohmic drop of the gold/CIM carbon/ISM electrode at the current reversal point is shown in the inset.

The potential stability of gold/CIM carbon/ISM electrodes was evaluated by chronopotentiometry, in which a constant current of +1 nA was applied to the working electrode for 60 s while recording the potential, followed by a constant current of −1 nA for another 60 s (Bobacka 1999). For comparison, gold/ISM electrodes without CIM carbon were also tested. As shown in FIG. 6, the gold/ISM electrodes are subject to potential drifts up to 0.9 mV/s because of the ill-defined phase boundary potential and low capacitance. When CIM carbon is used as the intermediate layer between the gold electrode and the ISM, the potential drift is significantly reduced to 1.0±0.2 µV/s (n=3), with an Ohmic drop of 0.36 mV for this 1 nA current. The capacitance of the electrode is calculated to be 1.0 mF, with a total resistance of 0.36 MΩ. Due to the high double-layer capacitance resulting from the interconnected mesopores of CIM carbon, gold/CIM carbon/ISM electrodes exhibit a higher capacitance than other SC-ISEs with valinomycin-doped membranes, such as the electrodes previously studied with interlayers of poly(3,4-ethylenedioxythiophene) (300 µF), carbon black with platinum nanoparticles (217 µF), graphene (83 µF), and carbon nanotubes (60 µF) (Bobacka 1999; Paczosa-Bator et al. 2013; Li et al. 2012).

Figure 9:
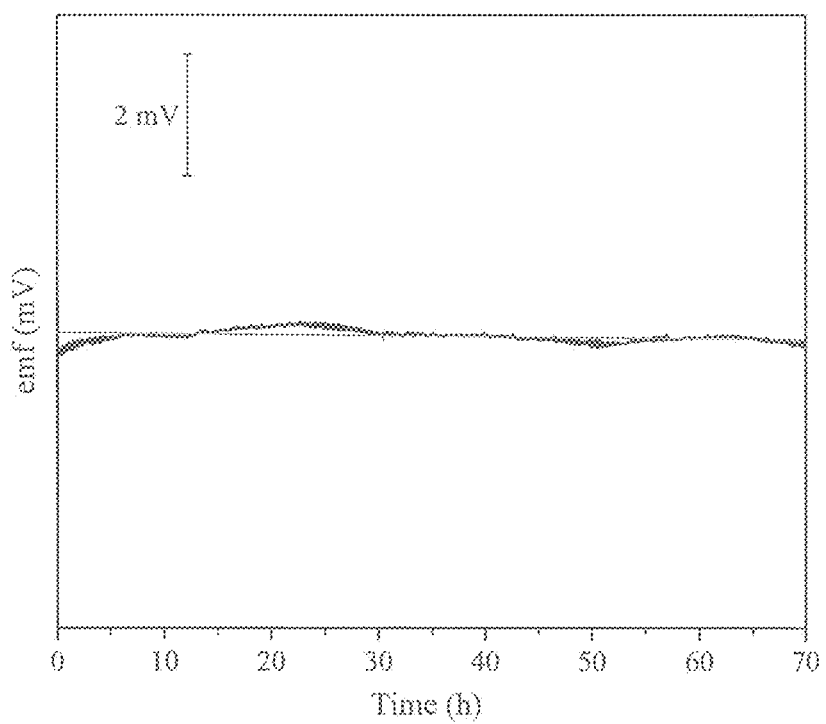
FIG. 9 is a graph of long-term stability of a gold/CIM carbon/ISM electrode measured in a 1 mM KCl solution at a constant temperature of 25° C. The emf response of the electrode is shown as the bold line, and the non-bold line is the linear fit of the raw data used for the long-term drift calculation.

Although chronopotentiometry shows on a short timescale a very good potential stability with a relatively large applied current (in comparison to the residual current in potentiometry), other factors such as a gradual decrease in adhesion between the ISM and the substrate might also lead to the deterioration of the electrode response on a longer timescale (Lindner et al. 1993). Therefore, long-term continuous tests of gold/CIM carbon/ISM electrodes were performed for 72 h in 1 mM KCl solution at a constant temperature of 25° C. using temperature-controlled samples. These experiments showed a long-term drift of 1.3±0.3 µV/h (n=3) for gold/CIM carbon/ISM electrodes (FIG. 9), making these electrodes the most stable SC-ISEs reported so far. The high double-layer capacitance of CIM carbon likely contributes to this superior electrochemical performance.

Example 3

Solid State Reference Electrode and Paper-Based Potentiometric Sensing Devices

Materials.

Reagents were obtained from the following sources: mesophase pitch from Mitsubishi Gas Chemicals (Tokyo, Japan), Ludox AS-40 colloidal silica from Sigma-Aldrich (St. Louis, Mo.), o-nitrophenyl octyl ether (o-NPOE) and high molecular weight poly(vinyl chloride) (PVC) from Fluka (Buchs, Switzerland), ionic liquid [$C_8$min+][$C_1C_1N^-$] from IOLITEC (Tuscaloosa, Ala.), Tecoflex SG-80A polyurethane from Thermedic Polymer Products (Woburn, Mass.), and AGCL-675 Ag/AgCl ink from Conductive Compounds (Hudson, N.H.). All chemicals were used as received without further purification. Deionized water was purified to a resistivity of 18.2 MΩ/cm with a Milli-Q PLUS reagent-grade water system (Millipore, Bedford, Mass.). CIM carbon and the redox couple consisting of [Co($C_9,C_9$-bipy)$_3$](TPFPB)$_2$ and [Co($C_9,C_9$-bipy)$_3$](TPFPB)$_3$ were prepared as in Examples 1 and 2.

Electrode Fabrication.

The 2 mm diameter gold disk electrodes (CH Instruments, Austin, Tex.) were polished over polishing cloths with aqueous dispersions of alumina (0.3 and 0.05 µm, Buehler, Lake Bluff, Ill.). They were cleaned by ultrasonication in water and ethanol and dried with a flow of argon. CIM carbon powder was manually ground for 5 min using a pestle. The CIM carbon suspension was prepared by ultrasonicating 47.5 mg of CIM carbon and 2.5 mg of PVC as binder in 1 mL of freshly distilled tetrahydrofuran (THF) for 30 min. An amount of 30 µL of the CIM carbon suspension was drop-cast onto the gold electrodes and left to dry, forming CIM carbon films with a thickness of approximately 200 µm.

Precursor solutions for reference membranes were prepared by dissolving in 2 mL of freshly distilled THF 60 mg the ionic liquid [$C_8$min+][$C_1C_1N^-$], 120 mg of PVC as polymeric matrix, and 120 mg of o-NPOE as plasticizer, as described before (Zhang et al. 2012). Moreover, 1.4 mmol/kg each of [Co($C_9,C_9$-bipy)$_3$](TPFPB)$_2$ and [Co($C_9,C_9$-bipy)$_3$](TPFPB)$_3$ was added to this solutions as an internal reference. The precursor solutions were stirred for 2 h to ensure complete dissolution.

To form reference membranes with a thickness of approximately 100 µm, two portions of the precursor solutions (20 µL, followed by 30 µL after 1 min) were drop-cast onto the CIM carbon layer on a gold electrode. The coated electrode was then mounted into a cylindrical body with a screw cap at the opposite end as shown in FIG. 1A. Prior to measurements, these electrodes were conditioned in a 1.0 mM NaCl solution for 1 h.

Fabrication of Paper-Based Cl⁻ Sensing Devices.

Paper-based sample zones and microfluidic channels were defined by patterning polyurethane lines that penetrated through the whole thickness of ashless filter papers (Whatman Grade 589/2 white ribbon). Approximately 2.5 g of polyurethane was dissolved in 40 mL of THF, and this solution was then applied to both sides of the paper using a capillary, forming polyurethane lines approximately 2 mm in width. The Ag/AgCl electrodes were patterned on paper by stencil printing. A hand-cut Frisket Film (low tack, Grafix, Maple Heights, Ohio) was used as the stencil and Ag/AgCl ink was applied to the openings of the stencil using a rubber brush, followed by a curing process at 100° C. for 15 min.

To form 2-mm wide reference membranes, a 5 µL microcapillary was used to apply the precursor solution onto paper. To ensure the full penetration of the membrane components through the entire thickness of the paper, the precursor solution was applied on both sides of the paper 4 times with a 1 min time interval between applications to allow THF to evaporate. A CIM carbon-reference membrane suspension was prepared by ultrasonicating for 30 min 60 mg of CIM carbon in 1 mL of the solution containing the reference membrane components. The resulting suspension was then applied onto paper using a capillary to form a homogenous mixture of CIM carbon and reference membrane, with an effort to maximize the contact area between this homogenous mixture and the reference membrane, which was applied separately.

Potentiometric Measurements.

Electrode potentials were measured with an EMF 16 potentiometer (input impedance 10 TΩ) controlled by EMF Suite 1.03 software (Lawson Labs, Malvern, Pa.). To test the electrochemical performance of the CIM carbon-based all-solid-state reference electrodes, a conventional double-junction external reference electrode (DX200, Mettler Toledo, Switzerland; 3.0 M KCl saturated with AgCl as inner filling solution and 1.0 M LiOAc as bridge electrolyte) was used. To test the response of paper-based Cl⁻ sensing devices, two copper alligator clips were used to connect the Ag/AgCl and CIM carbon electrodes to a potentiometer. All of the paper-based Cl⁻ sensing devices were used without preconditioning, i.e., without exposure of the Ag/AgCl electrode and the reference membrane to aqueous solutions prior to measurements. Activity coefficients were calculated according to a two-parameter Debye-Hückel approximation.

RESULTS AND DISCUSSION

Ionic Response of CIM Carbon-Based Reference Electrodes.

Figure 11:
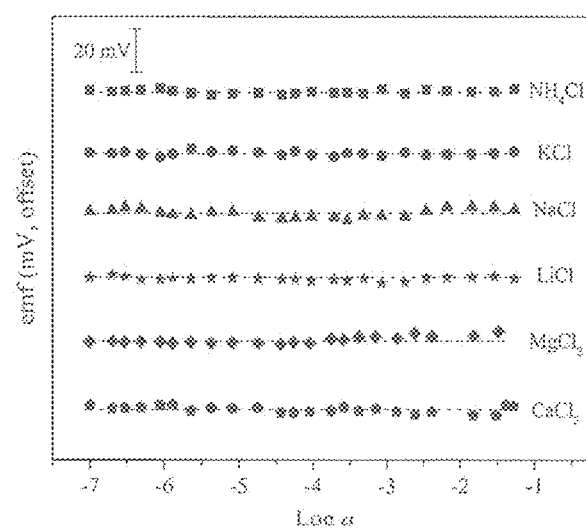
FIG. 11 is a graph of potentiometric responses of gold/CIM carbon/reference membrane electrodes in aqueous solutions of $NH_4Cl$, $KCl$, $NaCl$, $LiCl$, $MgCl_2$, and $CaCl_2$ in the concentration range from $10^{-7}$ M to $10^{-1}$ M. The responses were measured by addition of aliquots of concentrated salt solutions under continuous stirring. The response curves have been shifted vertically for clarity.

A good reference electrode should not respond to any sample species. All-solid-state reference electrodes consisting of a gold electrode coated with a CIM carbon layer and a reference membrane doped with the hydrophobic redox buffer $[Co(C_9,C_9\text{-bipy})_3]^{2+/3+}$ and the ionic liquid $[C_8min+][C_1C_1N^-]$ was tested and the ionic responses of such electrodes were measured against a conventional double-junction reference electrode. The resulting emf responses are shown in FIG. 11. Overall, the obtained calibration curve intercept, $E°$, is $-120.6\pm3.7$ mV for 3 electrodes, and for a given electrode, the $E°$ is $-120.8\pm8.0$ mV in 6 electrolytes. For each electrolyte, there is only a very small emf response of the CIM carbon-based reference electrodes in the concentration range from $10^{-7}$ M to $10^{-1}$ M, demonstrating the low potential variability of CIM carbon-based reference electrodes to ions with different charges and hydrophilicities. The change in emf over the entire range of activities is $1.9\pm0.8$ mV/decade for $NH_4$, $1.1\pm0.6$ mV/decade for $K^+$, $0.9\pm0.5$ mV/decade for $Na^+$, $0.9\pm0.6$ mV/decade for $Li^+$, $1.1\pm1.0$ mV/decade for $Mg^{2+}$, and $0.5\pm0.3$ mV/decade for $Ca^{2+}$ (n=3). This low dependence of the emf on the concentrations of ions is consistent with the phase boundary potential at the reference membrane/sample interface being defined by partitioning of the ionic liquid between the hydrophobic reference membrane phase and the aqueous sample phase. Unlike in the case of an ISE membrane, transfer of sample ions into the reference membrane is not occurring to an extent that it affects the phase boundary potential.

Use of CIM Carbon-Based Reference Electrodes to Measure Cl⁻ Responses of a Ag/AgCl ISE.

Figure 12:
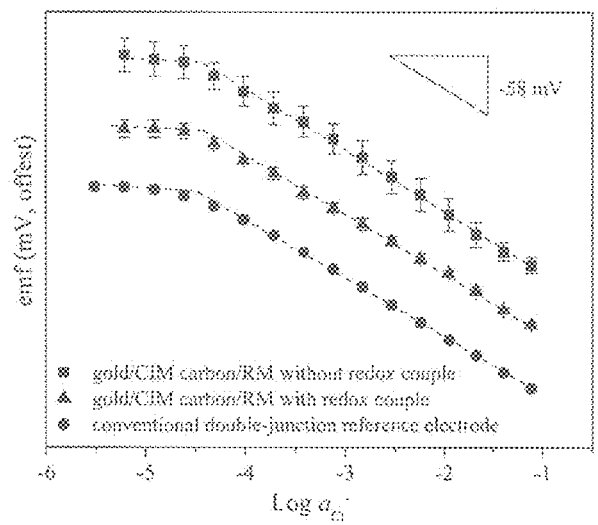
FIG. 12 is a graph of potentiometric responses to $Cl^-$ of a Ag/AgCl ISE against reference electrodes with different electrode configurations, i.e., gold/CIM carbon/reference membrane (RM) without redox couple, gold/CIM carbon/reference membrane with redox couple, and a commercial double-junction reference electrode. The response curves have been shifted vertically for clarity.

To assess the suitability and reproducibility of CIM carbon-based reference electrodes in ion-selective potentiometry, Cl⁻ measurements were performed with a AgCl-coated Ag wire as the ISE and two different reference electrode assemblies (i.e., gold/CIM carbon/reference membrane with or without redox couple). For comparison, a conventional double-junction reference electrode was also employed. The Cl⁻ responses were measured by successive dilution of a 0.1 M NaCl solution while monitoring the emf. The corresponding potentiometric Cl⁻ response characteristics are shown in FIG. 12 and summarized in Table 6.

TABLE 6

Potentiometric Cl⁻ Responses of a Ag/AgCl ISE vs. Reference Electrode Assemblies with a Reference Membrane (RM) or a Conventional Double Junction[a]

| reference electrode | slope (mV/decade) | E° (mV) | detection limit (M) |
|---|---|---|---|
| gold/CIM carbon/RM without redox couple | −57.7 ± 2.3 | 122.9 ± 12.9 | $10^{-4.4}$ |
| gold/CIM carbon/RM with redox couple | −55.5 ± 1.0 | 82.8 ± 2.8 | $10^{-4.4}$ |
| conventional double-junction | −55.9 | −12.1 | $10^{-4.5}$ |

[a]Means and standard deviations for five separate measurements with one Ag/AgCl ISE and five different reference electrodes. The E° values were obtained by extrapolation of the linear section of the emf response to a Cl⁻ activity of 1.0M.

As Table 6 shows, CIM carbon-based reference electrodes both with and without the hydrophobic redox couple yield Nernstian responses (i.e., $-55.5\pm1.0$ mV/decade with a reference membrane with the redox couple and $-57.7\pm2.3$ mV/decade when no redox couple was used), with values that are within error indistinguishable from the response slope obtained with a conventional double-junction reference electrode (i.e., $-55.9$ mV/decade). The detection limits obtained from these different reference electrodes were all approximately $10^{-4.4}$ M. These values are close to the intrinsic detection limit for Cl⁻ using a Ag/AgCl ISE (i.e., $10^{-4.9}$ M), which is determined by the solubility of AgCl.

Since there is no internal reference for the gold/CIM carbon/reference membrane electrodes without redox couple, the standard deviation of $E°$ (12.9 mV) is relatively large. This value is comparable to what has been observed in the past for many solid contact ISEs and is not necessarily problematic if devices are properly calibrated, but it is unsuitable for calibration-free measurements with disposable miniaturized sensing devices. The poor electrode-to-electrode repeatability can be significantly improved by doping the reference membrane with the hydrophobic redox couple $[Co(C_9,C_9\text{-bipy})_3]^{2+/3+}$, reducing the standard deviation of E to 2.8 mV.

Effects of Light, Oxygen, and Carbon Dioxide.

Light, $O_2$, and $CO_2$ have been reported to interfere with the response of some all-solid-state ISEs, and the possibility of such interferences should also be considered for all-solid-state reference electrodes. Generally, photosensitivity can be observed with conducting polymer and semiconductor solid contacts that have a suitable band gap. Interference caused by $CO_2$ can be attributed to changes in the pH of a water layer formed at the solid contact-membrane interface, and $O_2$ can interfere by forming an irreversible $O_2$ half-cell at the surface of the underlying electron conductor or by oxidizing functional groups on organic conductors.

The effect of light on gold/CIM carbon/reference membrane electrodes was investigated by continuously recording their emf values versus a conventional double-junction electrode while switching off and on the fluorescent tube lights in the laboratory. The effects of $O_2$ or $CO_2$ were tested by bubbling these gases into 1.0 mM NaCl sample solutions, followed by purging with Ar to remove those gases again. As shown in the top two traces of FIG. 13, no significant effects of light and $O_2$ were observed. While the insensitivity to light is due to the absence of a band gap of CIM carbon in the visible range, the excellent resistance to $O_2$ can be attributed to the low amounts of redox-active impurities and the absence of functional groups on the surface of CIM carbon.

Figure 13:
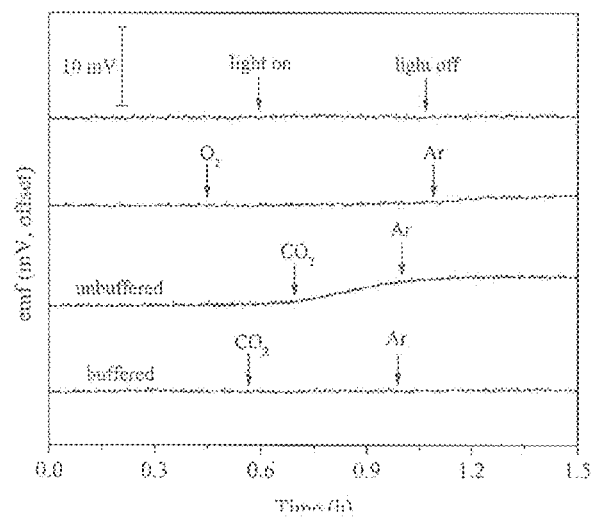
FIG. 13 is a graph of effects of light, $O_2$, and $CO_2$ on the potential stability of gold/CIM carbon/reference membrane electrodes. The effect of $CO_2$ was studied both in an unbuffered 1.0 mM NaCl solution and a 0.1 M phosphate buffer solution (pH 7.5). The response curves have been shifted vertically for clarity.

When CIM carbon-based reference electrodes were exposed to $CO_2$ in an unbuffered solution, however, a potential drift of 9.5 mV/h is observed (FIG. 13, $3^{rd}$ trace from the top). This drift can be attributed to a decrease of the solution pH, promoting the co-ion extraction of $H^+$ and the ionic liquid anion, $[C_1C_1N^-]$ into the reference membrane. This affects the phase boundary potential at the reference membrane-sample interface, as we have reported previously.[28] This effect, combined with fluctuations in the stir rate, may have affected the noise level of the data shown in FIG. 11. To eliminate this effect and make it possible to study the influence of $CO_2$ on the CIM carbon-reference membrane interface, a phosphate buffer (pH=7.5) was used, stabilizing the pH of the sample solution. As shown in the bottom trace of FIG. 13, no significant effect of $CO_2$ is observed with this pH buffered sample system, demonstrating the excellent resistance of the CIM carbon-reference membrane interface to $CO_2$. Use of an ionic liquid that is less subject to protonation would enable the construction of CIM carbon-based reference electrodes with resistance to $CO_2$ in pH unbuffered solutions.

Long-Term Potential Stability.

Figure 10:
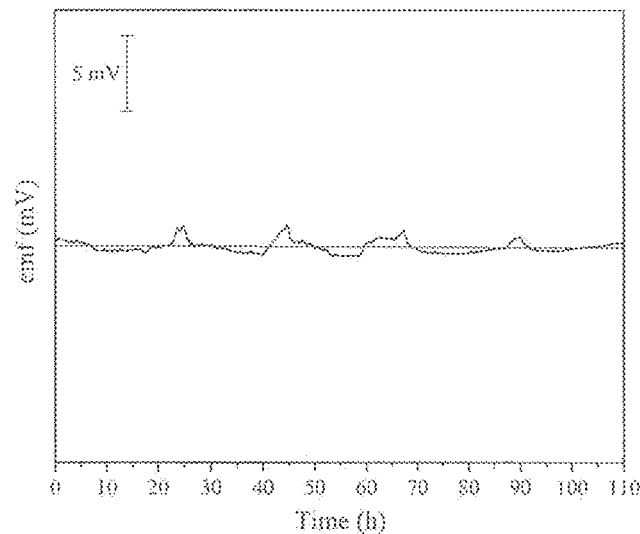
FIG. 10 is a graph of potential stability of a gold/CIM carbon/reference membrane (RM) electrode without redox couple, measured in a 1 mM NaCl solution at a constant temperature of 25° C. The emf response of the electrode is shown along with the linear fit of the raw data used for the emf drift calculation.

Potential stability is another important aspect for all-solid-state ISEs and reference electrodes, especially when they are used to continuously monitor the concentration of an analyte over an extended period of time. In this study, the potential stability of CIM carbon-based reference electrodes was assessed by monitoring the potentials of these references electrodes continuously for 110 h in a 1.0 mM NaCl solution at a constant temperature of 25° C. (see FIG. 10). To avoid leaching of the redox couple from the reference membrane into the sample as a cause of potential drifts, gold/CIM carbon/reference membrane electrodes without redox couple were used. Due to the large double-layer capacitance of the CIM carbon layer, the potential drift of these reference electrodes was as low as $1.7\pm1.2$ μV/h (n=3), which is on the same level as for CIM carbon-based ISEs (i.e., $1.3\pm0.3$ μV/h). For measurements that require long-term potential stability with high $E°$ reproducibility, a more hydrophobic redox couple or a redox couple covalently attached to the polymer backbone could be employed.

Design of Disposable Paper-Based Potentiometric $Cl^-$ Sensing Devices.

Because they combine affordability, scalability, simplicity, and flexibility, paper-based analytical devices have recently attracted much attention. In particular, miniaturized potentiometric $Cl^-$ sensing devices were fabricated on wax-printed paper, with two stencil-printed Ag/AgCl electrodes serving as the ISE and the reference electrode. These devices resembled the one shown in FIG. 14a but had a wax rather than a polyurethane barrier to contain aqueous solutions. For measurements, one droplet each of the sample and a reference electrolyte solution had to be applied onto the paper close to the corresponding electrodes, resulting in spontaneous wicking of the two liquids into the central contacting area to complete the electric circuit. While these $Cl^-$ sensing devices have the advantage of being simple to use, they are subject to sample dependent liquid junction potentials at the sample/reference electrolyte interface and require the manual application of not only the sample but also a reference electrolyte solution.

To further simplify these paper-based potentiometric sensing devices and improve their accuracy, CIM carbon-based reference electrodes were used in this work to replace the conventional Ag/AgCl reference electrodes. Three designs were tested in a step-by-step approach to the final device. To start, a design similar to the one used for the previously reported paper-based $Cl^-$ sensing devices, i.e., with two stencil-printed Ag/AgCl electrodes, was used (FIG. 14a). However, instead of printed wax, polyurethane was used to form the hydrophobic barriers that define the microfluidic channels. Polyurethane was chosen not only because it is inexpensive, readily commercially available, and can be inkjet-printed for mass fabrication, but also because its use avoids the melting process that is required to fabricate wax-printed paper devices. In a second step, to eliminate the liquid junction potentials at the sample/reference electrolyte interface, a reference membrane was integrated into the central zone of the device, as shown in FIG. 14b. Finally, a CIM carbon-reference membrane reference system was used to replace the conventional Ag/AgCl reference electrode (FIG. 14c).

Use of a Reference Membrane to Eliminate Liquid Junction Potentials in Paper-Based Potentiometric $Cl^-$ Sensing Devices.

To assess the effectiveness of reference membranes to eliminate the liquid junction potentials in paper-based potentiometric $Cl^-$ sensing devices, $Cl^-$ measurements were performed using a 1.0 M LiCi reference electrolyte and sample solutions containing different LiCl concentrations. LiCl was chosen here on purpose because of the large difference in the ionic mobilities of $Li^+$ and $Cl^-$, which results in liquid junction potentials as large as tens of millivolts. This offered the advantage that pinholes through the paper-supported reference membrane, which would have compromised the intended use of the reference membranes, would have been readily recognized by the occurrence of large liquid junction potentials within such pinholes.

Figure 15:
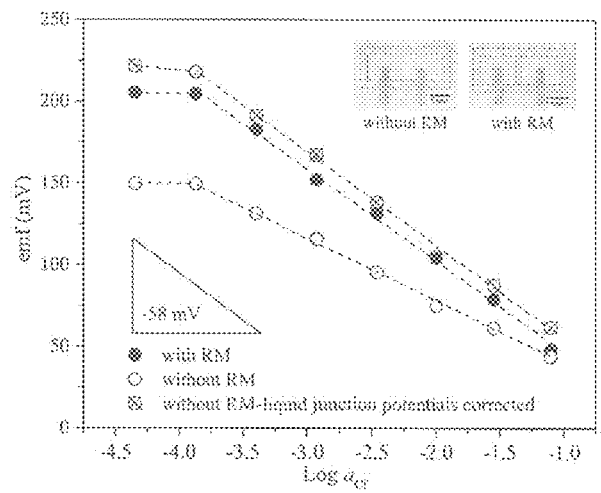
FIG. 15 is a graph of a comparison of the response to LiCi of paper-based potentiometric $Cl^-$ sensing devices with and without reference membranes (RMs). The open and crossed circles represent the emf of the paper-based potentiometric $Cl^-$ sensing device without a reference membrane before (open circles) and after (crossed circles) subtraction of the calculated liquid junction potential. The solid circles represent the emf of the paper-based potentiometric $Cl^-$ sensing device with a reference membrane without any mathematical manipulation. Photographs of the two types of devices are shown on the top right.

As shown in the lower trace of FIG. 15 (open circles), the $Cl^-$ sensing devices without reference membranes (as shown in FIG. 14a) exhibit a sub-Nernstian response with a slope of $-38.8\pm1.3$ mV/decade, while their counterparts with reference membranes (FIG. 14b) yielded a Nernstian response with a slope of $-57.1\pm1.5$ mV/decade in the range from $10^{-1.0}$ to $10^{-3.5}$ M (solid circles). The inferior response slope of the $Cl^-$ sensing devices without reference membranes could be improved by mathematically correcting liquid junction potentials using the Henderson equation, as illustrated in the top trace in FIG. 15 (crossed circles). The corrected response slope of $-57.0\pm1.3$ mV/decade matches with the results for the devices with reference membranes, which demonstrates that the behavior of the system is well understood. However, corrections of liquid junction potentials are not readily possible for real samples with complex and unknown compositions.

Integration of a CIM Carbon-Reference Membrane Reference System into Paper-Based Potentiometric $Cl^-$ Sensing Devices.

Figure 16:
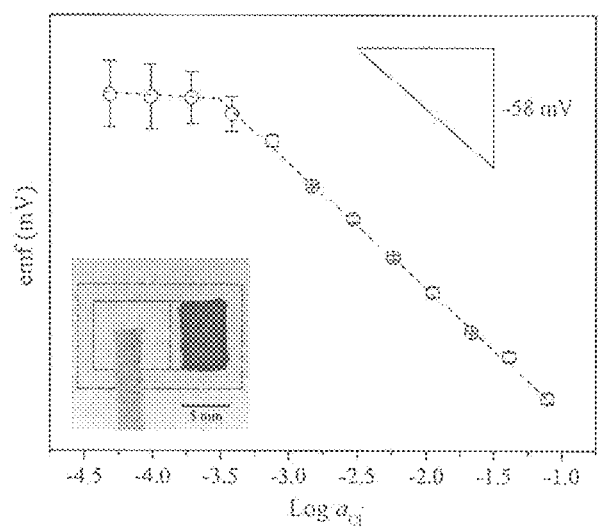
FIG. 16 is a graph of a potentiometric $Cl^-$ response curve of paper-based potentiometric $Cl^-$ sensing devices containing a Ag/AgCl ISE and a CIM carbon-based reference electrode with a reference membrane. A photograph of the device is shown on the bottom left. The average and standard deviation of each data point is based on measurements with three individual devices.

The use of these disposable paper-based $Cl^-$ sensing devices can be further simplified by employing an all-solid-state CIM carbon-based reference electrode to replace the conventional Ag/AgCl reference electrode, eliminating the reference electrolyte (FIG. 14c). To test their electrochemical performance, 10 μL aliquots of sample solution containing different concentrations of NaCl were applied to the area around the Ag/AgCl ISE. The resulting $Cl^-$ response curve is shown in FIG. 16. In this potentiometric cell, all phase boundary potentials are well defined. Specifically, the phase boundary potential between the sample and Ag/AgCl is defined by the redox reaction $AgCl(s)+e^-\leftrightarrows Ag(s)+Cl^-(aq)$, the phase boundary potential at the sample/reference membrane interface is defined by the ionic liquid, and the phase boundary potential at the reference membrane/CIM carbon interface is defined by the redox couple. As a result, these paper-based $Cl^-$ sensing devices exhibit a highly reproducible Nernstian response with a slope of $-59.8\pm0.9$ mV/decade and a $E°$ of $19.8\pm2.1$ mV over the range from $10^{-1.0}$ to $10^{-3.5}$ M. This demonstrates that CIM carbon-based reference systems can be successfully integrated into miniaturized potentiometric systems based on paper.

Figure 18:
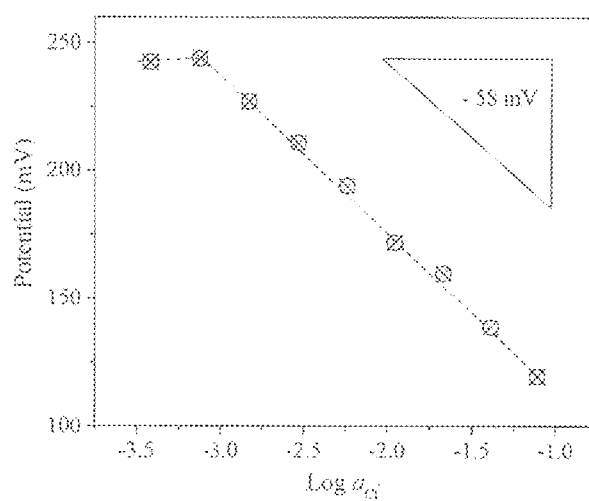
FIG. 18 is a potentiometric $Cl^-$ response curve of paper-based potentiometric sensing device containing CIM carbon-based SC-ISE and SS-reference electrode.

Paper-based potentiometric sensing device containing both a CIM carbon-based SC-ISE and a SS-reference electrode was fabricated in a similar way as the devices with stencil-printed Ag/AgCl electrodes and CIM carbon-based SS-reference electrodes (see FIG. 17). An anion-exchange membrane with CIM carbon was used as the SC-ISE to generate a potentiometric response to anions. To use these sensing devices, one droplet of sample was applied to the sample zone area and the potential difference between the two carbon electrodes was measured. As FIG. 18 shows, these devices exhibited Nernstian responses to the Cl⁻ anions in the range from about $10^{-1.0}$ to $10^{-3.0}$ M, with a slope of −61.3 mV/decade.

This example has demonstrated that CIM carbon can be used as a solid contact material to fabricate all-solid-state reference electrodes. This permits the construction of high-performance all-solid-state potentiometric ISEs and reference electrodes with the same type of solid contact, polymer matrix, fabrication process, and electrode configuration. CIM carbon-based reference electrodes exhibit a very low dependence of the half-cell potential in solutions of various electrolytes with concentrations in a wide range. Due to the low amounts of redox-active impurities on the surface of CIM carbon, phase boundary potentials at the membrane/CIM carbon interfaces can be defined well by the $[Co(C_9, C_9\text{-bipy})_3]^{2+/3+}$ redox couple, permitting a high electrode-to-electrode reproducibility of E°. The interconnected mesopores of CIM carbon offer the added advantage of a high double-layer capacitance, resulting in potential drifts as low as 1.7 µV/h and making these electrodes the most stable all-solid-state reference electrodes reported so far.

CIM carbon-based reference system can be integrated into a disposable paper-based potentiometric Cl⁻ sensing device, replacing the conventional Ag/AgCl reference electrode, eliminating the need for reference electrolyte, and eliminating liquid junction potentials. These miniaturized Cl⁻ sensing devices with CIM carbon-based reference systems are inexpensive, easy to handle, and offer very reproducible Cl⁻ measurements with sample volumes as low as 10 µL.

Although the present invention has been described with reference to preferred embodiments, workers skilled in the art will recognize that changes may be made in form and detail without departing from the spirit and scope of the invention.

What is claimed is:

1. A solid contact electrode comprising a solid electron conductor, an interlayer comprising mesoporous carbon and a membrane, wherein the interlayer is in contact with the conductor and the membrane, wherein the mesoporous carbon is colloid-imprinted mesoporous (CIM) carbon having an oxygen content of less than 2% by weight.

2. The solid contact electrode of claim 1 wherein the CIM carbon is imprinted with colloidal silica.

3. The solid contact electrode of claim 1 wherein the average diameter of the mesopores in the CIM carbon is between about 2 nm and about 50 nm.

4. The solid contact electrode of claim 1 wherein the solid electron conductor comprises gold, platinum, silver, copper, stainless steel, carbon, indium-tin-oxide (ITO), fluorine-doped tin oxide (FTO) or aluminum.

5. The solid contact electrode of claim 1 wherein the electrode is an ion-selective electrode and the membrane is an ion-selective membrane.

6. The solid contact electrode of claim 1 wherein the electrode is a reference electrode and the membrane is a reference membrane.

7. An electrochemical sensor system comprising one or more electrodes, wherein at least one of the electrodes is a solid-contact electrode comprising CIM carbon having an oxygen content of less than 2% by weight.

8. The electrochemical sensor system of claim 7 wherein the CIM carbon is imprinted with colloidal silica.

9. The electrochemical sensor system of claim 7 wherein the pores in the CIM carbon have an average diameter between about 2 nm and about 50 nm.

10. The electrochemical sensor system of claim 7 wherein the system comprises 2, 3 or 4 solid-contact electrodes.

11. The electrochemical sensor system of claim 7 wherein the solid-contact electrode comprises a solid electron conductor.

12. The electrochemical sensor system of claim 11 wherein the solid electron conductor is gold, platinum, silver, copper, stainless steel, carbon, indium-tin-oxide (ITO), fluorine-doped tin oxide (FTO) or aluminum.

13. The electrochemical sensor system of claim 7 wherein one of the solid-contact electrodes is an ion-selective electrode and further comprises an ion-selective membrane.

14. The electrochemical sensor system of claim 7 wherein one of the solid-contact electrodes is a reference electrode and further comprises a reference membrane.

15. The electrochemical sensor system of claim 10 wherein one of the solid-contact electrodes is a reference electrode and a second solid-contact electrode is an ion-selective electrode, wherein the reference electrode further comprises a solid electron conductor and a reference membrane and the ion-selective electrode further comprises a solid electron conductor and an ion-selective membrane.

16. The electrochemical sensor system of claim 7, wherein the system is a paper-based electrochemical system comprising a reference electrode and an ion-selective electrode.

17. The electrochemical sensor system of claim 16 wherein the solid-contact electrode is the reference electrode comprising CIM carbon and the ion-selective electrode is a stencil printed Ag/AgCl electrode and the analyte to be tested is chloride.

18. The electrochemical sensor system of claim 16 comprising two solid-contact electrodes, wherein the first solid-contact electrode is the reference electrode and the second solid-contact electrode is the ion-selective electrode.

19. The electrochemical sensor system of claim 7, wherein the analyte is selected from $H^+$, $Li^+$, $Na^+$, $K^+$, $Mg^{2+}$, $Ca^{2+}$, $Cu^{2+}$, $Ag^+$, $Zn^{2+}$, $Cd^{2+}$, $Hg^{2+}$, $Pb^{2+}$, $NH_4^+$, carbonate, bicarbonate, nitrate, nitrite, sulfide, chloride, iodide, heparin, protamine, and combinations thereof.

20. A method of making a solid-contact electrode comprising: forming an interlayer comprising CIM carbon over a solid electron conductor, wherein the CIM carbon has an oxygen content of less than 2% by weight; and
   placing a membrane over the interlayer wherein the interlayer is disposed between and in contact with the solid electron conductor and the membrane.

21. The method of claim 20 wherein the carbon interlayer comprises a film with a thickness between about 0.5 µm and about 1000 µm.

22. The method of claim 20 wherein the interlayer is formed by a method comprising making a suspension of the CIM carbon powder and using the suspension of the CIM carbon to form a thin film over a solid electron conductor.

23. The method of claim 20 wherein the average diameter of the mesopores in the carbon interlayer is between about 2 nm and about 50 nm.

24. The method of claim 20 wherein the solid-contact electrode is an ion selective electrode and the membrane is an ion-selective membrane.

25. The method of claim 20 wherein the solid-contact electrode is a reference electrode and the membrane is a reference membrane.

26. A method of measuring an analyte in a sample comprising: placing the sample in contact with an ion-selective electrode in an electrochemical system, the electrochemical system comprising at least one solid-contact electrode, wherein the solid-contact electrode comprises a solid electron conductor, CIM carbon interlayer and a membrane, wherein the CIM carbon has an oxygen content of less than 2% by weight.

27. The method of claim 26 wherein the at least one solid-contact electrode is the ion-selective electrode.

28. The method of claim 26 wherein the at least one solid contact electrode is a reference electrode.

29. The method of claim 26, wherein the analyte is selected from $H^+$, $Li^+$, $Na^+$, $K^+$, $Mg^{2+}$, $Ca^{2+}$, $Cu^{2+}$, $Ag^+$, $Zn^{2+}$, $Cd^{2+}$, $Hg^{2+}$, $NH_4^+$, carbonate, bicarbonate, nitrate, nitrite, sulfide, chloride, iodide, heparin, protamine, and combinations thereof.

30. The method of claim 26 wherein the sample is a clinical sample, an industrial sample, a forensic sample, an agricultural sample or an environmental sample.

31. The method of claim 26 wherein the electrochemical system comprises a sensor, wherein the sensor is a potentiometric sensor, ion-sensitive field effect transistor, a voltammetric sensor, an amperometric sensor, a coulometric sensor, or an impedance sensor.

32. The method of claim 31 wherein the method further comprises correlating the results from the sensor to determine the quantity or concentration of the analyte.

* * * * *